US009012399B2

(12) United States Patent
Cao et al.

(10) Patent No.: US 9,012,399 B2
(45) Date of Patent: Apr. 21, 2015

(54) CONTROLLED RELEASE OF GROWTH FACTORS AND SIGNALING MOLECULES FOR PROMOTING ANGIOGENESIS

(75) Inventors: Lan Cao, Stoughton, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/992,617

(22) PCT Filed: Jun. 1, 2009

(86) PCT No.: PCT/US2009/045856
§ 371 (c)(1),
(2), (4) Date: Jan. 6, 2011

(87) PCT Pub. No.: WO2009/146456
PCT Pub. Date: Dec. 3, 2009

(65) Prior Publication Data
US 2011/0117170 A1 May 19, 2011

Related U.S. Application Data

(60) Provisional application No. 61/130,486, filed on May 30, 2008.

(51) Int. Cl.
A61K 38/18 (2006.01)
A61K 9/00 (2006.01)
A61K 45/06 (2006.01)
A61L 27/54 (2006.01)

(52) U.S. Cl.
CPC ............. *A61K 45/06* (2013.01); *A61K 38/1866* (2013.01); *A61K 38/1858* (2013.01); *A61L 27/54* (2013.01); *A61L 2300/412* (2013.01); *A61L 2300/414* (2013.01); *A61L 2300/426* (2013.01); *A61L 2300/432* (2013.01); *A61L 2300/45* (2013.01); *A61L 2300/602* (2013.01)

(58) Field of Classification Search
None
See application file for complete search history.

(56) References Cited

U.S. PATENT DOCUMENTS

| 5,073,627 | A | 12/1991 | Curtis et al. |
|---|---|---|---|
| 5,885,829 | A | 3/1999 | Mooney et al. |
| 6,193,970 | B1 | 2/2001 | Pardoll et al. |
| 6,251,396 | B1 | 6/2001 | Gaur et al. |
| 6,281,256 | B1 | 8/2001 | Harris et al. |
| 6,403,374 | B1 | 6/2002 | Tsien et al. |
| 6,429,199 | B1 | 8/2002 | Krieg et al. |
| 6,511,650 | B1 | 1/2003 | Eiselt et al. |
| 6,541,022 | B1 | 4/2003 | Murphy et al. |
| 6,642,363 | B1 | 11/2003 | Mooney et al. |
| 6,685,963 | B1 | 2/2004 | Taupin et al. |
| 6,748,954 | B2 | 6/2004 | Lee et al. |
| 6,767,928 | B1 | 7/2004 | Murphy et al. |
| 6,783,712 | B2 | 8/2004 | Slivka et al. |
| 6,790,840 | B1 | 9/2004 | Lee et al. |
| 6,797,738 | B2 | 9/2004 | Harris et al. |
| 6,800,733 | B2 | 10/2004 | Tsien et al. |
| 7,157,566 | B2 | 1/2007 | Tsien et al. |
| 7,186,413 | B2 | 3/2007 | Bouhadir et al. |
| 7,192,693 | B2 | 3/2007 | Bryant et al. |
| 7,427,602 | B1 | 9/2008 | Shea et al. |
| 7,575,759 | B2 | 8/2009 | Murphy et al. |
| 7,790,699 | B2 * | 9/2010 | Melvik et al. ............... 514/54 |
| 8,067,237 | B2 | 11/2011 | Mooney et al. |
| 8,188,058 | B2 | 5/2012 | Hackam et al. |
| 8,273,373 | B2 | 9/2012 | Alsberg et al. |
| 8,728,456 | B2 | 5/2014 | Sands et al. |
| 2002/0131853 | A1 | 9/2002 | Nagasawa |
| 2002/0150604 | A1 | 10/2002 | Yi et al. |
| 2003/0075822 | A1 | 4/2003 | Slivka et al. |
| 2003/0082806 | A1 | 5/2003 | Berenson et al. |
| 2003/0095994 | A1 | 5/2003 | Geistlich et al. |
| 2003/0100527 | A1 | 5/2003 | Krieg et al. |
| 2004/0058883 | A1 | 3/2004 | Phillips et al. |
| 2004/0063206 | A1 | 4/2004 | Rowley et al. |
| 2004/0136968 | A1 | 7/2004 | Zheng et al. |
| 2004/0151764 | A1 | 8/2004 | Zamora |
| 2004/0220111 | A1 | 11/2004 | Kleinman et al. |
| 2004/0242469 | A1 | 12/2004 | Lee et al. |
| 2004/0242482 | A1 | 12/2004 | Gehring et al. |
| 2005/0002915 | A1 | 1/2005 | Atala et al. |
| 2005/0053667 | A1 | 3/2005 | Irvine et al. |
| 2005/0079159 | A1 | 4/2005 | Shastri et al. |

(Continued)

FOREIGN PATENT DOCUMENTS

| EP | 0562862 A1 | 9/1993 |
|---|---|---|
| EP | 1452191 A2 | 9/2004 |

(Continued)

OTHER PUBLICATIONS

Cao et al. "Promoting Angiogenesis Via Manipulation of VEGF Responsiveness with Notch Signaling." Biomaterials 30:4085-4093 (2009).
Richardson et al. "Polymeric System for Dual Growth Factor Delivery." Nature Biotechnology. 19(11):1029-34 (2001).
"Antigens and Receptors." *Immunology*. Doan et al., eds. Philadelphia: Wolters Kluwer/Lippincott Williams & Wilsons. (2008):11-23.
Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171. 10(2003):4984-4989.

(Continued)

*Primary Examiner* — Marianne P Allen
(74) *Attorney, Agent, or Firm* — Mintz Levin Cohn Ferris Glovsky and Popeo, P.C.; Ingrid A. Beattie

(57) ABSTRACT

The present invention comprises compositions, methods, and devices for delivering angiogenic factors and signaling molecules to a target tissue, and controlling the release of these factors and signaling molecules to spatially and temporally restrict their release and dissemination, for the purpose of promoting angiogenesis in target tissues.

29 Claims, 11 Drawing Sheets

(56) References Cited

U.S. PATENT DOCUMENTS

| | | | |
|---|---|---|---|
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2006/0083712 A1 | 4/2006 | Anversa |
| 2006/0264380 A1 | 11/2006 | Hellstrom et al. |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0138416 A1 | 6/2008 | Rauh et al. |
| 2008/0206308 A1 | 8/2008 | Jabbari et al. |
| 2008/0268052 A1 | 10/2008 | Voytik-Harbin et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0020216 A1 | 1/2011 | Mooney et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0329791 A1 | 12/2012 | Ashwell et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0234423 A1 | 8/2014 | Sands et al. |

FOREIGN PATENT DOCUMENTS

| | | | |
|---|---|---|---|
| EP | 1561481 A2 | 8/2005 |
| WO | WO-9616086 A1 | 5/1996 |
| WO | WO-9812228 A1 | 3/1998 |
| WO | WO-9951259 A2 | 10/1999 |
| WO | WO-0135932 A2 | 5/2001 |
| WO | WO-03020884 A2 | 3/2003 |
| WO | WO-2004006990 A2 | 1/2004 |
| WO | WO-2004030706 A2 | 4/2004 |
| WO | WO-2004089413 A1 | 10/2004 |
| WO | WO-2005026318 A2 | 3/2005 |
| WO | WO-2005037190 A2 | 4/2005 |
| WO | WO-2005037293 A1 | 4/2005 |
| WO | WO-2005072088 A2 | 8/2005 |
| WO | WO-2006119619 A1 | 11/2006 |
| WO | WO-2006136905 A2 | 12/2006 |
| WO | WO-2007030901 A1 | 3/2007 |
| WO | WO-2007064152 A1 | 6/2007 |
| WO | WO-2007070660 A2 | 6/2007 |
| WO | WO-2007078196 A1 | 7/2007 |
| WO | WO-2007150020 A1 | 12/2007 |
| WO | WO-2008018707 A1 | 2/2008 |
| WO | WO-2009002401 A2 | 12/2008 |
| WO | WO-2009005769 A2 | 1/2009 |
| WO | WO-2009074341 A1 | 6/2009 |
| WO | WO-2009102465 A2 | 8/2009 |
| WO | WO-2009146456 A1 | 12/2009 |
| WO | WO-2009155583 A1 | 12/2009 |
| WO | WO-2010120749 A2 | 10/2010 |
| WO | WO-2011014871 A1 | 2/2011 |
| WO | WO-2011063336 A2 | 5/2011 |
| WO | WO-2011109834 A2 | 9/2011 |
| WO | WO-2011130753 A2 | 10/2011 |
| WO | WO-2011150240 A1 | 12/2011 |
| WO | WO-2011151431 A1 | 12/2011 |
| WO | WO-2011163669 A2 | 12/2011 |
| WO | WO-2012009611 A2 | 1/2012 |
| WO | WO-2012048165 A2 | 4/2012 |
| WO | WO-2012064697 A2 | 5/2012 |
| WO | WO-2012148684 A1 | 11/2012 |
| WO | WO-2012149358 A1 | 11/2012 |
| WO | WO-2012167230 A1 | 12/2012 |
| WO | WO-2013106852 A1 | 7/2013 |
| WO | WO-2013158673 A1 | 10/2013 |

OTHER PUBLICATIONS

Akira et al. "Pathogen Recognition and Innate Immunity." *Cell*. 124. 4(2006):783-801.

Akira et al. "Toll-Like Receptors: Critical Proteins Linking Innate and Acquired Immunity." *Nat. Immunol.* 2.8(2001):675-680.

Aldhous. "Print Me a Heart and a Set of Arteries." *New Scientist*. 2547(2006):19.

Ali et al. "Controlled Local Delivery of GM-CSF From Polymer-Based Vaccines Enhances Anti-Tumor Immune Responses by Priming Host Dendritic Cells." *2007 AACR Annual Meeting*. 48(2007):652. (Abstract #2736).

Ali et al. "Converging Cell Therapy with Biomaterials." *Cell Transplantation from Laboratory to Clinic*. Burlington, MA: Elsevier, Inc. (2006):591-609.

Ali et al. "In situ Regulation of DC Subsets and T Cells Mediates Tumor Regression in Mice." *Sci. Transl. Med.* 1.8(2009):8-19.

Ali et al. "Infection-Mimicking Materials to Program Dendritic Cells in situ." *Nat. Mater.* 8.2(2009):151-158.

Ali et al. "Sustained GM-CSF and PEI Condensed pDNA Presentation Increases the Level and Duration of Gene Expression in Dendritic Cells." *J. Control. Release*. 132.3(2008):273-278.

Allen et al. "Regulation of Satellite Cells During Skeletal Muscle Growth and Development." *Proc. Soc. Exp. Biol. Med.* 194.2(1990):81-86.

Allen et al. "Regulation of Skeletal Muscle Satellite Cell Proliferation by Bovine Pituitary Fibroblast Growth Factor." *Exp. Cell Res.* 152.1(1984):154-160.

Almarza et al. "Evaluation of Three Growth Factors in Combination of Two for Temporomandibular Joint Disc Tissue Engineering." *Arch. Oral Biol.* 51.3(2006):215-221.

Alsberg et al. "Cell-Interactive Alginate Hydrogels for Bone Tissue Engineering." *J. Dent. Res.* 80.11(2001):2025-2029.

Alsberg et al. "Engineering Growing Tissues." *PNAS*. 99.18(2002):12025-12030.

Anderson et al. "The NOD Mouse: A Model of Immune Dysregulation." *Annu. Rev. Immunol.* 23(2005):447-485.

Anderson. "A Role for Nitric Oxide in Muscle Repair: Nitric Oxide-Mediated Activation of Muscle Satellite Cells." *Mol. Biol. Cell.* 11(2000):1859-1874.

Arany et al. "At the Edge of Translation—Materials to Program Cells for Directed Differentiation." *Oral Dis.* 17.3(2011):241-251.

Atala et al. "Endoscopic Treatment of Vesicoureteral Reflux with a Chondrocyte-Alginate Suspension." *J. Urol.* 152(1994):641-643.

Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.

Badovinac et al. "Regulation of CD8 T+ Cells Undergoing Primary and Secondary Responses to Infection in the Same Host." *J. Immunol.* 170(2003):4933-4942.

Bakri et al. "Pharmacokinetics of Intravitreal Bevacizumab (Avastin)." *Ophthalmology*. 114.5(2007):855-859.

Banchereau et al. "Dendritic Cells and the Control of Immunity." *Nature*. 392.6673(1998):245-252.

(56) References Cited

OTHER PUBLICATIONS

Barbero et al. "Growth Factor Supplemented Matrigel Improves Ectopic Skeletal Muscle Formation—A Cell Therapy Approach." *J. Cell. Physiol.* 186(2001):186-192.
Barrio et al. "A Two-Dimensional Numerical Study of Spatial Pattern Formation in Interacting Turing Systems." *Bull. Math Biol.* 61.3(1999):483-505.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Bischoff. "Proliferation of Muscle Satellite Cells on Intact Myofibers in Culture." *Dev. Biol.* 115.1(1986):129-139.
Blanes et al. "Induction of Autoimmune Diabetes by Oral Administration of Autoantigen." *Science.* 274.5293(1996):1707-1709.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brouwers et al. "Can the Growth Factors PTHrP, Ihh and VEGF, Together Regulate the Development of a Long Bone?" *J. Biomech.* 39.15(2006):2774-2782.
Burdick et al. "Stimulation of Neurite Outgrowth by Neurotrophins Delivered From Degradable Hydrogels." *Biomater.* 27.3(2006):452-459.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi. "Replacement Organs, Hot Off the Press." *New Scientist.* 177.2379(2003):16.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.

Conboy et al. "The Regulation of Notch Signaling Controls Satellite Cell Activation and Cell Fate Determination in Postnatal Myogenesis." *Dev. Cell.* 3.3(2002):397-409.
Conn et al. "Purification of a Glycoprotein Vascular Endothelial Cell Mitogen from a Rat Glioma-Derived Cell Line." *PNAS.* 87.4(1990):1323-1327.
Cooper et al. "Extended Amplification In Vitro and Replicative Senescence: Key Factors Implicated in the Success of Human Myoblast Transplantation." *Hum. Gene Ther.* 14(2003):1169-1179.
Cornelison et al. "Single-Cell Analysis of Regulatory Gene Expression in Quiescent and Activated Mouse Skeletal Muscle Satellite Cells." *Dev. Biol.* 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1(2001):79-94.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.
De Temmerman et al. "Particulate Vaccines: On the Quest for Optimal Delivery and Immune Response." *Drug Disc. Today.* 16.13/14(2011):569-582.
den Haan et al. "CD8+ by not CD8− Dendritic Cells Cross-Prime Cytotoxic T Cells In Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered In vitro." *In Vitro Cell Dev. Biol. Anim.* 36.5(2000):327-335.
Dieu et al. "Selective Recruitment of Immature and Mature Dendritic Cells by Distinct Chemokines Expressed in Different Anatomic Sites." *J. Exp. Med.* 188.2(1988):373-386.
Dor et al. "Making Vascular Networks in the Adult: Branching Morphogenesis Without a Roadmap." *Trends Cell Biol.* 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.
Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.
Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature.* 419.6904(2002):304-308.

(56) References Cited

OTHER PUBLICATIONS

Eldar et al. "Self-Enhanced Ligand Degradation Underlies Robustness of Morphogen Gradients." *Dev. Cell.* 5.4(2003):635-646.
Engler et al. "Matrix Elasticity Directs Stem Cell Lingeage Specification." *Cell.* 126.4(2006):677-689.
Ennett et al. "Temporally Regulated Delivery of VEGF in vitro and in vivo." *J. Biomed. Mater. Res. A.* 79.1(2006):176-184.
Faissner et al. "Boundaries and Inhibitory Molecules in Developing Neural Tissues." *Glia.* 13.4(1995):233-254.
Farrar et al. "T Helper Subset Development: Roles of Instruction, Selection, and Transcription." *J. Clin. Invest.* 109.4(2002):431-435.
Ferrara et al. "Angiogenesis as a Therapeutic Target." *Nature.* 438.7070(2005):967-974.
Ferrara et al. "Discovery and Development of Bevacizumab, an Anti-VEGF Antibody for Treating Cancer." *Nat. Rev. Drug Discov.* 3.5(2004):391-400.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG46721.1, Jun. 29, 2004.
GenBank Accession No. CBI71013.1, Feb. 2, 2010.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngot Head Neck Surg.*130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol.* 39(1995):845-854.
Gussoni et al. "Dystrophin Expression and in the *mdx* Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.

(56) References Cited

OTHER PUBLICATIONS

Hashimoto et al. "Development of Alginate Wound Dressings Linked with Hybrid Peptides Derived from Laminin and Elastin." *Biomaterials*. 25.7-8(2004):1407-1414.
Hawke et al. "Myogenic Satellite Cells: Physiology to Molecular Biology." *J. Appl. Physiol*. 91(2001):534-551.
Helm et al. "Synergy Between Interstitial Flow and VEGF Directs Capillary Morphogenesis in vitro Through a Gradient Amplification Mechanism." *PNAS*. 102.44(2005):15779-15784.
Henry et al. "The VIVA Trial: Vascular Endothelial Growth Factor in Ischemia for Vascular Angiogenesis." *Circulation*. 107.10(2003):1359-1365.
Hermanson. *Bioconjugate Techniques*. New York: Academic Press. (1996):152-185.
Heslop et al. "Transplanted Primary Neonatal Myoblasts can Give Rise to Functional Satellite Cells as Identified Using the Myf5nlacZl+ Mouse." *Gene Ther*. 8(2001):778-783.
Hildner et al. "*Batf3* Deficiency Reveals a Critical Role for CD8α+30 Dendritic Cells in Cytotoxic T Cell Immunity." *Science*. 322.5904(2008):1097-1100.
Hill et al. "Designing Scaffolds to Enhance Transplanted Myoblast Survival and Migration." *Tissue Engin*. 12.5(2006):1295-1304.
Hill et al. "Muscle Satellite (Stem) Cell Activation During Local Tissue Injury and Repair." *J. Anat*. 203.1(2003):89-99.
Hill. "Macroporous Scaffold Architecture, Peptide, HGF/FGF and Myoblast Incorporation Enhance Myogenesis." *IADR/AADR/CADR 83rd General Session*. (Mar. 9-12, 2005). Poster #2829.
Hirano et al. "Peptide and Protein Presenting Materials for Tissue Engineering." *Adv. Mat*. 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS*. 95.23(1998):13806-13811.
Hodi et al. "Immunologic and Clinical Effects of Antibody Blockade of Cytotoxic T Lymphocyte—Associated Antigen 4 in Previously Vaccinated Cancer Patients." *PNAS*. 105.8(2008):3005-3010.
Horsley et al. "IL-4 Acts as a Myoblast Recruitment Factor During Mammalian Muscle Growth." *Cell*. 113.4(2003):483-494.
Hsiong et al. "Differentiation Stage Alters Matrix Control of Stem Cells." *J. Biomed. Mater. Res. Part A*. 8(2007):145-156.
Huang et al. "Fabrication and in vitro Testing of Polymeric Delivery Systems for Condensed DNA." *J. Biomed. Mater. Res*. 67(2003):1384-1392.
Huang et al. "Long-Term in Vivo Gene Expression via Delivery of PEI-DNA Condensates From Porous Polymer Scaffolds." *Hum. Gene Ther*. 16.5(2005):609-617.
Hubbell et al. "Materials Engineering for Immunomodulation." *Nature*. 462(2009):449-460.
Hubbell. "Biomaterials in Tissue Engineering." *Bio/Tech*. 13(1995):565-576.
Huebsch et al. "Harnessing Traction-Mediated Manipulation of the Cell/Matrix Interface to Control Stem-Cell Fate." *Nat. Mater*. 9.6(2010):518-526.
Ishihara et al. "Roles of Bradykinin in Vascular Permeability and Angiogenesis in Solid Tumor." *Int. Immunopharmacol*. 2.4(2002):499-509.
Jain. "Molecular Regulation of Vessel Maturation." *Nat. Med*. 9.6(2003):685-693.
Jain. "The Manufacturing Techniques of Various Drug Loaded Biodegradable Poly(lactide-co-glycolide) (PLGA) Devices." *Biomater*. 21.23(2000):2475-2490.
Jankovic et al., "In the Absence of IL-12, CD4+ T Cell Responses to Intracellular Pathogens Fail to Default to a Th2 Pattern and are Host Protective in an IL-10-/- Setting." *Immunity*. 16.3(2002):429-439.
Jego et al. "Plasmacytoid Dendritic Cells Induce Plasma Cell Diffferenetiation Through Type I Interferon and Interleukin 6." *Immunity*. 19.2(2003):225-234.
Jiang et al. "Self-Organization of Periodic Patterns by Dissociated Feather Mesenchymal Cells and the Regulation of Size, Number and Spacing of Primorida." *Development*. 126.22(1999):4997-5009.
Jinushi et al. "Enhancing the Clinical Activity of Granulocyte-Macrophage Colony-Stimulating Factor-Secreting Tumor Cell Vaccines." *Immunol. Rev*. 222(2008):287-298.
Jinushi et al. "MFG-E8-Mediated Uptake of Apoptotic Cells by APCs Links the Pro- and Antiinflammatory Activities of GM-CSF." *J. Clin. Invest*. 117.7(2007):1902-1913.
Johnson et al. "Activation of Skeletal Muscle Satellite Cells and the Role of Fibroblast Growth Factor Receptors." *Exp. Cell Res*. 219.2(1995):449-453.
Kanzler et al. "Therapeutic Targeting of Innate Immunity with Toll-Like Receptor Agaonists and Antagonists." *Nat. Med*. 13.5(2007):552-559.
Kawai et al. "Innate Immune Recognition of Viral Infection." *Nat. Immunol*. 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release*. 62.1-2(1999):279-287.
Kim et al. "An Overview of Cartilage Tissue Engineering." *Yonsei Med. J*. 41.6(2000):766-773.
Kinoshita et al. "Successive Injections in MDX Mice of Myoblasts Grown with bFGF." *Neuromusc. Disord*. 6.3(1996):187-193.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kisak et al. "The Vesosome—A Multicompartment Drug Delivery Vehicle." *Curr. Med. Chem*. 11.2(2004):199-219.
Klebanoff et al. "CD8+ T-Cell Memory in Tumor Immunology and Immunotherapy." *Immunol. Rev*. 211(2006):214-224.
Klinman. "Immunotherapeutic Uses of CpG Oligodeoxynucleotides." *Nat. Rev. Immunol*. 4.4(2004):249-258.
Kondo et al. "A Reaction-Diffusion Wave on the Skin of the Marine Angelfish *Pomacanthus*." *Nature*. 376(2002):765-768.
Kong et al. "Controlling Rigidity and Degradation of Alginate Hydrogels via Molecular Weight Distribution." *Biomacromolec*. 5.5(2004):1720-1727.
Kong et al. "Designing Alginate Hydrogels to Maintain Viability of Immobilized Cells." *Biomat*. 24.22(2003):4023-4029.
Kong et al. "Non-Viral Gene Delivery Regulated by Stiffness of Cell Adhesion Substrates." *Nat. Mater*. 4(2005):406-410.
Krieg. "Development of TLR9 Agonists for Cancer Therapy." *J. Clin. Invest*. 117.5(2007):1184-1194.
Kumamoto et al. "Induction of Tumor-Specific Protective Immunity by in situ Langerhans Cell Vaccine." *Nat. BioTechnol*. 20.1(2002):64-69.
Kumar et al. "Toll-Like Receptors and Innate Immunity." *Biochem. Biophys. Res. Commun*. 388.4(2009):621-625.
Kurts et al. "CD8 T Cell Ignorance or Tolerance to Islet Antigens Depends on Antigen Dose." *PNAS*. 96.22(1999):12703-12707.
Kwon et al. "In vivo Targeting Dendritic Cells for Activation of Cellular Immunity Using Vaccine Carriers Based on pH-Responsive Microparticles." *PNAS*. 102.51(2005):18264-18268.
Langer et al. "Tissue Engineering." *Science*. 260(1993):920-926.
Lanzavecchia et al. "Regulation of T Cell Immunity by Dendritic Cells." *Cell*. 106.3(2001):263-266.
Leach et al. "Coating of VEGF-Releasing Scaffolds with Bioactive Glass for Angiogenesis and Bone Regeneration." *Biomater*. 27.17(2006):3249-3255.
Lee et al. "Hydrogel Formation via Vell Crosslinking." *Adv. Mat*. 15.21(2003):1828-1832.
Lee et al. "Hydrogels for Tissue Engineering." *Chem. Rev*. 101.7(2001):1869-1879.
Lefaucheur et al. "The Cellular Events of Injured Muscle Regeneration Depend on the Nature of the Injury." *Neuromusc. Disorders*. 5.6(1995):501-509.
Lensch et al. "Scientific and Clinical Opportunities for Modeling Blood Disorders With Embryonic Stem Cells." *Blood*. 107.7(2006):2605-2612.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol*. 184(2000):101-109.

(56) References Cited

OTHER PUBLICATIONS

Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-α is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu. "Dendritic Cell Subsets and Lineages, and Their Functions in Innate and Adaptive Immunity." *Cell.* 106.3(2001):259-262.
Lu et al. "Muscle-Derived Stem Cells Seeded Into Acellular Scaffolds Develop Calcium—Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292. 5520(2001):1389-1394.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin αvβ3-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-β Superfamily Member." *Nature.* 387(1997):83-90.
Melero-Martin et al. "Engineering Robust and Functional Vascular Networks in Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151. 3(1992):497-505.
Moser et al. "Dendritic Cell Regulation of TH1-TH2 Regulation." *Nat. Immunol.* 1.3(2000):199-205.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Noguera-Troise et al. "Blockade of Dll4 Inhibits Tumour Growth by Promoting Non-Productive Angiogenesis." *Nature.* 444. 7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337. 6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor α Gene Expression in Respiratory and Peripheral Muscles." *Arch. Bronconeumol.* 38.7(2002):311-316. (Spanish Original and English Abstract).
Partridge et al. "Conversion of mdx Myofibres From Dystrophin-Negative to -Positive by Injection of Normal Myoblasts." *Nature.* 337(1989):176-179.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.

(56) References Cited

OTHER PUBLICATIONS

Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to Listeria monocytogenes Infection." *J. Immunol.* 166(2001):3402-3409.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets in Vivo." *J. Immunol.* 165(2000):566-572.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181 (1992):87-140.
Rapraeger. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.* 10(1998):366. (Abstract #153.07).
Richards Grayson et al. "Multi-Pulse Drug Delivery From a Resorbable Polymeric Microchip Device." *Nat. Mater.* 2.11(2003):767-772.
Riddle et al. "Role of Poly(lactide-co-glycolide) Particle Size on Gas-Foamed Scaffolds." *J. Biomater. Sci. Polym. Ed.* 15.12(2004):1561-1570.
Ridgway et al. "Inhibition of DII4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity in vitro and in vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Facilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Salvador et al. "Combination of Immune Stimulating Adjuvants With Poly(lactide-co-glycolide) Microspheres Enhances the Immune Response of Vaccines." *Vaccine.* 30.3(2011):589-596.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell.* 102.6(2000):777-786.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Skokos et al. "CD8-DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.

(56) References Cited

OTHER PUBLICATIONS

Sun et al. "Sustained Vascular Endothelial Growth Factor Delivery Enhances Angiogenesis and Perfusion in Ischemic Hind Limb." *Pharm. Res.* 22.7(2005):1110-1116.

Takeshita et al. "Therapeutic Angiogenesis." *J. Clin. Invest.* 93.2(1994):662-670.

Tamura et al. "Immunotherapy of Tumors with Autologous Tumor-Derived Heat Shock Protein Preparations." *Science.* 278.3(1997):117-120.

Tatsumi et al. "HGF/SF Is Present in Normal Adult Skeletal Muscle and Is Capable of Activating Satellite Cells." *Dev. Biol.* 194.1(1998):114-128.

Thurston et al. "The Delta Paradox: DLL4 Blockade Leads to More Tumour Vessels but Less Tumour Growth." *Nat. Rev. Cancer.* 7.5(2007):327-331.

Tidball. "Inflammatory Cell Response to Acute Muscle Injury." *Med. Sci. Sports Exerc.* 27.7(1995):1022-1032.

Turing. "Discussion: Turing's Theory of Morphogenesis—It's Influence on Modelling Biological Pattern and Form." *Bull. Math. Biol.* 52.1-2(1990):119-159.

Turing. "The Chemical Basis of Morphogenesis." *Philosophical Transactions of the Royal Society of London. Series B.* 237.641(1952):37-72.

Uchida et al. "Immunization by Particle Bombardment of Antigen-Loaded poly-(DL-lactide-co-glycolide) Microspheres in Mice." *Vaccine.* 12(2006):2120-2130.

Urbanek et al. "Stem Cell Niches in the Adult Mouse Heart." *PNAS.* 103.24(2006):9226-9231.

Van Duin et al. "Triggering TLR Signaling in Vaccination." *Trends Immunol.* 27.1(2006):49-55.

Vandenburgh et al. "Tissue-Engineered Skeletal Muscle Organoids for Reversible Gene Therapy." *Hum. Gene Ther.* 17(1996):2195-2200.

Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.

Vieira et al. "The Half-Lives of Serum Immunoglobulins in Adult Mice." *Eur. J. Immunol.* 18.2(1988):313-316.

Villadangos et al. "Intrinsic and Cooperative Antigen-Presenting Functions of Dendritic-Cell Subsets in vivo." *Nat. Rev. Immunol.* 7.7(2007):543-555.

Villadangos. "Presentation of Antigens by MHC Class II Molecules: Getting the Most Out of Them." *Molec. Immunol.* 38.5(2001):329-346.

Von Dassow et al. "The Segment Polarity Network is a Robust Developmental Module." *Nature.* 406.6792(2000):188-192.

Wakim et al. "Dendritic Cell-Induced Memory T Cell Activation in Nonlymphoid Tissues." *Science.* 319(2008):198-202.

Waldron-Lynch et al. "Advances in Type 1 Diabetes Therapeutics: Immunomodulation and β-Cell Savage." *Endocrinol. Metab. Clin. North Am.* 38.2(2009):303-317.

Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.

Wang et al. "Biological Activity of Bevacizumab, a Humanized Anti-VEGF Antibody in vitro." *Angiogenesis.* 7.4(2004):335-345.

Wei et al. "Global Mapping of H3K4me3 and H3K27me3 Reveals Specificity in Plasticity in Lineage Fate Determination of Differentiating CD4+ T Cells." *Immunity.* 30.1(2009):155-167.

Wernig et al. "Function of Skeletal Muscle Tissue Formed After Myoblast Transplantation into Irradiated Mouse Muscles." *J. Physiol.* 522.2(2000):333-345.

White et al. "Leukemia Inhibitory Factor Enhances Regeneration in Skeletal Muscles After Myoblast Transplantation." *Musc. Nerve.* 24.5(2001):695-697.

World Health Organization. "Global Burden of Musculoskeletal Disease Revealed in new WHO Report." *Bull. World Health Organ.* 81.11(2003):853-854.

World Health Organization. "The World Health Report 2004: Changing History." *The World Health Report.* (2004):1-169.

Wright et al. "Muscle-Based Gene Therapy and Tissue Engineering for the Musculoskeletal System." *Drug Disc. Today.* 6.14(2001):728-733.

Yancopoulos et al. "Vascular-Specific Growth Factors and Blood Vessel Formation." *Nature.* 407.6801(2000):242-248.

Yuen et al. "Mimicking Nature by Codelivery of Stimulant and Inhibitor to Create Temporally Stable and Spatially Restricted Angiogenic Zones." *PNAS.* 107.42(2010):17933-17938.

Zammit et al. "Kinetics of Myoblast Proliferation Show That Resident Satellite Cells are Competent to Fully Regenerate Skeletal Muscle Fibers." *Exp. Cell Res.* 281.1(2002):39-49.

Zammit et al. "Muscle Satellite Cells Adopt Divergent Fates: A Mechanism for Self-Renewal?" *J. Cell Biol.* 166.3(2004):347-357.

Zeltinger et al. "Effect of Pore Size and Void Fraction on Cellular Adhesion, Proliferation, and Matrix Deposition." *Tissue Eng.* 7.5(2001):557-572.

Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.

Zhao et al. "Active Scaffolds for On-Demand Drug and Cell Delivery." *PNAS.* 108.1(2011):67-72.

Zhao et al. "Directed Cell Migration via Chemoattractants Released from Degradable Microspheres." *Biomat.* 26(2005):5048-5063.

Zhou et al. "Microstructure and Mechanical Properties of Poly(L-lactide) Scaffolds Fabricated by Gelatin Particle Leaching Method." *J. Appl. Polymer Sci.* 98(2005):1373-1379.

"Transient." Merriam-Webster Dictionary. Web. Jul. 18, 2014. www.merriam-webster.com/dictionary/transient.

"Wound Management: Past, Present, and Future." *Clinicians' Pocket Guide to Chronic Wound Repair.* Mulder et al., eds. Springhouse, PA: Springhouse Corporation. (1998):85-90.

Alsberg et al. "Regulating Bone Formation via Controlled Scaffold Design." *J. Dent. Res.* 82.11(2003):903-908.

Anderson et al. "Biomaterial Microarrays: Rapid, Microscale Screening of Polymer-Cell Interaction." *Biomaterials.* 26.23(2005):4892-4897.

Anderson et al. "Nanoliter-Scale Synthesis of Arrayed Biomaterials and Application to Human Embryonic Stem Cells." *Nat. Biotechnol.* 22.7(2004):863-866.

Augst et al. "Alginate Hydrogels as Biomaterials." *Macromol. Biosci.* 6(2006):623-633.

Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.

Balakrishna et al. "Structural Correlates of Antibacterial and Membrane-Permeabilizing Activities in Acylpolyamines." *Antimicrob. Agents Chemother.* 50.3(2006):852-861.

Bar-Cohen et al. "Electroactive Polymer Actuators and Sensors." *MRS Bullet.* 33.3(2008):173-181.

Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.

Bates. "Improved Muscle Regeneration by Combining VEGF With IGF1." *Regen. Med.* 5.6(2010):853-854.

Beaucage et al. "The Functionalization of Oligonucleotides Via Phosphoramidite Derivatives." *Tetrahedron.* 49.10(1993):1925-1963.

Beebe et al. "Functional Hydrogel Structures for Autonomous Flow Control Inside Microfluidic Channels." *Nature.* 404(2000):588-590.

Bekiari et al. "Study of Poly(N,N-dimethylacrylamide)/CdS Nanocomposite Organic/Inorganic Gels." *Langmuir.* 20.19(2004):7972-7975.

Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.

Boontheekul et al. "Controlling Alginate Gel Degradation Utilizing Partial Oxidation and Bimodal Molecular Weight Distribution." *Biomaterials.* 26.15(2005):2455-2465.

(56) References Cited

OTHER PUBLICATIONS

Bouhadir et al. "Degradation of Partially Oxidized Alginate and its Potential Application for Tissue Engineering." *Biotechnol. Prog.* 17.5(2001):945-950.
Brinkmann et al. "Neutrophil Extracellular Traps Kill Bacteria." *Science.* 303.5663(2004):1532-1535.
Bryant et al. "Photo-Patterning of Porous Hydrogels for Tissue Engineering." *Biomater.* 28.19(2007):2978-2986.
Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Comisar et al. "Engineering RGD Nanopatterned Hydrogels to Control Preosteoblast Behavior: A Combined Computational and Experimental Approach." *Biomaterials.* 28(2007):4409-4417.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.
Coulson et al. "Flow of Fluids through Granular Beds and Packed Columns." *Chemical Engineering.* New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Dar et al. "Optimization of Cardiac Cell Seeding and Distribution in 3D Porous Alginate Scaffolds." *Biotechnol. Bioeng.* 80(2002):305-312.
Doan et al. "Subcellular Localization of a Sporulation Membrane Protein is Achieved Through a Network of Interactions Along and Across the Septum." *Mol. Microbiol.* 55.6(2005):1767-1781.
Egholm et al. "Peptide Nucleic Acids (PNA). Oligonucleotide Analogues with an Achiral Peptide Backbone." *J. Am. Chem. Soc.* 114.5(1992):1895-1897.
Egholm et al. "PNA Hybridizes to Complementary Oligonucleotides Obeying the Watson-Crick Hydrogen-Bonding Rules." *Nature.* 365.6446(1993):566-568.
Falsey et al. "Peptide and Small Molecule Microarray for High Throughput Cell Adhesion and Functional Assays." *Bioconjug. Chem.* 12.3(2001):346-353.
Fischer et al. "A Brilliant Monomeric Red Fluorescent Protein to Visualize Cytoskeleton Dynamics in Dictyostelium." *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Fox. "Management of Worsening Multiple Sclerosis with Mitoxantrone: A Review." *Clin. Ther.* 28.4(2006):461-474.
GenBank Accession No. AA144040, Mar. 18, 2009.
GenBank Accession No. CAG29322.1, Oct. 16, 2008.
GenBank Accession No. CAG33149.1, Oct. 21, 2008.
GenBank Accession No. EF064765.1, Nov. 13, 2006.
Glasbey et al. "Image Analysis and Three-Dimensional Modelling of Pores in Soil Aggregates." *Eur. J. Soil Sci.* 42.2(1991):479-486.
Gupta et al. "Magnetically Controlled Targeted Micro-Carrier Systems." *Life Sci.* 44.3(1989):175-186.
Heath. "Cells for Tissue Engineering." *Trends Biotechnol.* 18.1(2006):17-19.
Hwang et al. "Fabrication of Three-Dimensional Porous Cell-Laden Hydrogel for Tissue Engineering." *Biofabrication.* 2.3(2010):035003.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).

Juntanon et al. "Electrically Controlled Release of Sulfosalicylic Acid from Crosslinked Poly(Vinyl Alcohol) Hydrogel." *Int. J. Pharm.* 356(2008):1-11.
Khownium et al. "Novel Endotoxin-Compounds with Terephthalaldehyde-bis-guanylihydrazone Scaffolds." *Bioorg. Med. Chem. Lett.* 16(2006):1305-1308.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.
Kong et al. "Controlling Degradation of Hydrogels via the Size of Crosslinked Junctions." *Adv. Mater.* 16.21(2004):1917-1921.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid Dna." *Pharma. Res.* 25.5(2008):1230-1238.
Kwon et al. "Electrically Erodible Polymer Gel for Controlled Release of Drugs." *Nature.* 354(1991):291-293.
Langenkamp et al. "Kinetics of Dendritic Cell Activation: Impact on Priming of TH1, TH2 and Nonpolarized T Cells." *Nat. Immunol.* 1.4(2000):311-316.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8a+ DCs and Human BDCA3+ DCs are Major Producers of IFN-λ in Response to Poly IC." *J. Exp. Med.* 207.12(2010):2703-2717.
Leor et al. "Cells, Scaffolds, and Molecules for Myocardial Tissue Engineering." *Pharmacol. Therapeutics.* 105(2005):151-163.
Letsinger et al. "Phosphoramidate Analogs of Oligonucleotides." *J. Org. Chem.* 35.11(1970):3800-3803.
Liu et al. "Nanostructured Materials Designed for Cell Binding and Transduction." *Biomacromolecules.* 2.2(2001):362-368.
Lutolf et al. "Repair of Bone Defects Using Synthetic Mimetics of Collagenous Extracellular Matrices." *Nat. Biotechnol.* 21.5(2003):513-518.
López et al. "Magnetic Applications of Polymer Gels." *Macromol. Symp.* 166.1(2001):173-178.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Meier et al. "Peptide Nucleic Acids (PNAs)—Unusual Properties of Noionic Oligonucleotide Analogues." *Angew. Chem. Int. Ed.* 31.8(1992):1008-1010.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Miller et al. "Lipopolysaccharide Sequestrants: Structural Correlates of Activity and Toxicity in Novel Acylhomospermines." *J. Med. Chem.* 48(2005):2589-2599.
Miyata et al. "Biomolecule-Sensitive Hydrogels." *Adv. Drug Deliv. Rev.* 54.1(2002):79-98.
Mohan et al. "Novel Porous, Polysaccharide Scaffolds for Tissue Engineering Applications." *Trends Biomater. Artif. Organs.* 18.2(2005):219-224.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
NCBI Accession No. NM_004119, Apr. 14, 2013.
NCBI Accession No. NM_006274.2, Mar. 31, 2013.
Niamlang et al. "Electrically Controlled Release of Salicylic Acid from poly(p-phenylene vinylene) Polyacrylamide Hydrogels." *Int. J. Pharm.* 371(2009):126-133.
Ohashi et al. "Surgical Excision Combined with Autologous Whole Tumor Cell Vaccination is an Effective Therapy for Murine Neuroblastoma." *J. Ped. Surg.* 41(2006):1361-1368.
Orner et al. "Arrays for the Combinatorial Exploration of Cell Adhesion." *J. Am. Chem. Soc.* 126.35(2004):10808-10809.

(56) References Cited

OTHER PUBLICATIONS

Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Pedersen et al. "Induction of Regulatory Dendritic Cells by Desamethasone and 1α,25-Dihydroxyvitamin D3." *Immunol. Lett.* 91(2004):63-69.
Porter et al. "Separation of Natural Populations of Coliform Bacteria from Freshwater and Sewage by Magnetic-Bead Cell Sorting." *J. Microbiol. Meth.* 33.3(1998):221-226.
Qui et al. "Environment-Sensitive Hydrogels for Drug Delivery." *Adv. Drug Deliv. Rev.* 53.3(2001):321-339.
Reis e Sousa. "Activation of Dendritic Cells: Translating Innate into Adaptive Immunity." *Curr. Opin. Immunol.* 16.1(3005):21-25.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Rizzo et al. "An Improved Cyan Fluorescent Protein Variant Useful for Fret." *Nat. Biotechnol.* 22.4(2004):445-449.
Salem et al. "Defining the Antigen-Specific T-Cell Response to Vaccination and Poly(I:C)/TLR3 Signaling." *J. Immunother.* 28.3(2005):220-228.
Salvay et al. "Inductive Tissue Engineering with Protein and DNA-Releasing Scaffolds." *Mol. Biosyst.* 2.1(2006):36-48.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Scheel et al. "Toll-Like Receptor-Dependent Activation of Several Human Blood Cell Types by Protamine Condensed mRNA." *Eur. J. Immunol.* 35(2005):1557-1566.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.
Shoichet et al. "Stability of Hydrogels Used in Cell Encapsulation: An In Vitro Comparison of Alginate and Agarose." *Biotechnol. Bioeng.* 50(1996):374-381.
Silva et al. "Material-Based Deployment Enhances Efficacy of Endothelial Progenitor Cells." *PNAS.* 105.38(2008):14347-14352.
Takahashi et al. "Induction of Pluripotent Stem Cells from Adult Human Fibroblasts by Defined Factors." *Cell.* 131.5(2007):861-872.
Tanaka et al. "Collapse of Gels in an Electric Field." *Science.* 218(1982):467-469.
Ten Dijke et al. "Growth Factors for Wound Healing." *Nat. Biotechnol.* 7(1989):793-798.
Tomer et al. "Electrically Controlled Release of Macromolecules from Cross-Linked Hyaluronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.
Ugarte et al. "Notch Signaling Enhances Osteogenic Differentiation While Inhibiting Adipogenesis in Primary Human Bone Marrow Stromal Cells." *Exp. Hematol.* 37(2009):867-875.
Wang et al. "Evolution of New Nonantibody Proteins via Iterative Somatic Hypermutation." *PNAS.* 101.48(2004):16745-16749.
Xie et al. "Preparation and Application of Surface-Coated Superparamagnetic Nanobeads in the Isolation of Genomic DNA." *J. Magn. Magnetic Mater.* 277.1(2004):16-23.
Yu et al. "Induced Pluripotent Stem Cell Lines Derived from Human Somatic Cells." *Science.* 318.5858(2007):1917-1920.
Yuk et al. "Electric Current-Sensitive Drug Delivery System Using Sodium Alginate/Polyacrylic Acid Composites." *Pharm. Res.* 9.7(1992):955-957.

\* cited by examiner

FIGURE 5
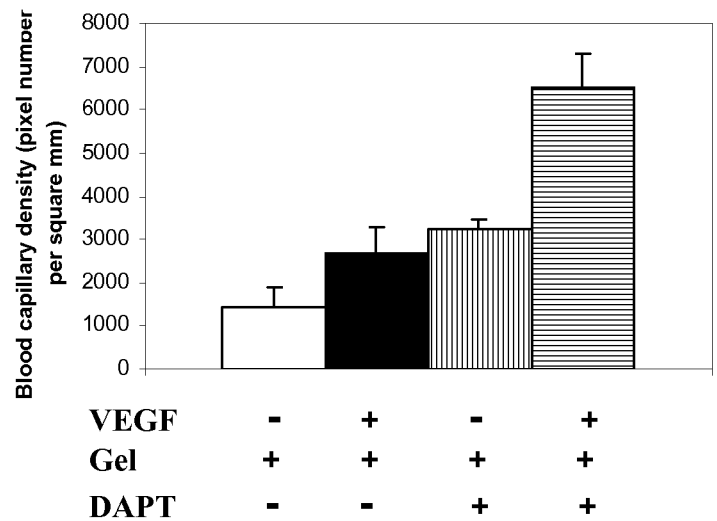
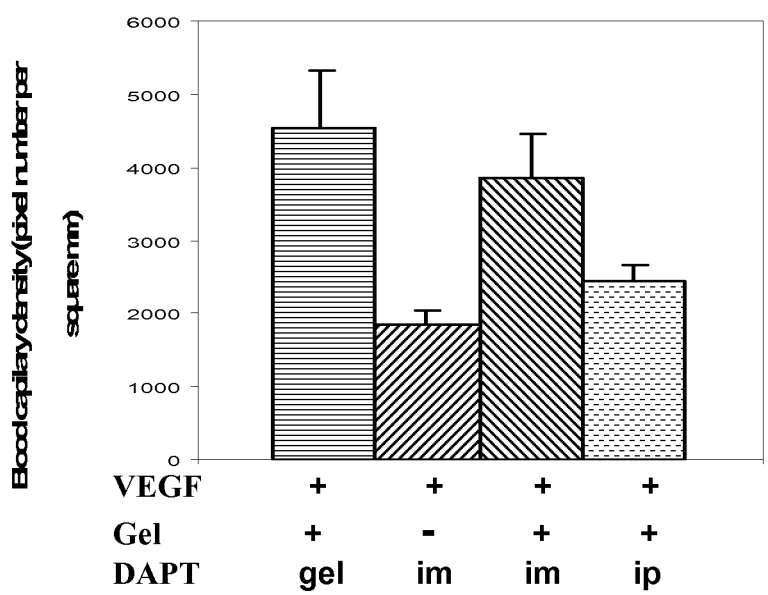

FIGURE 7
A
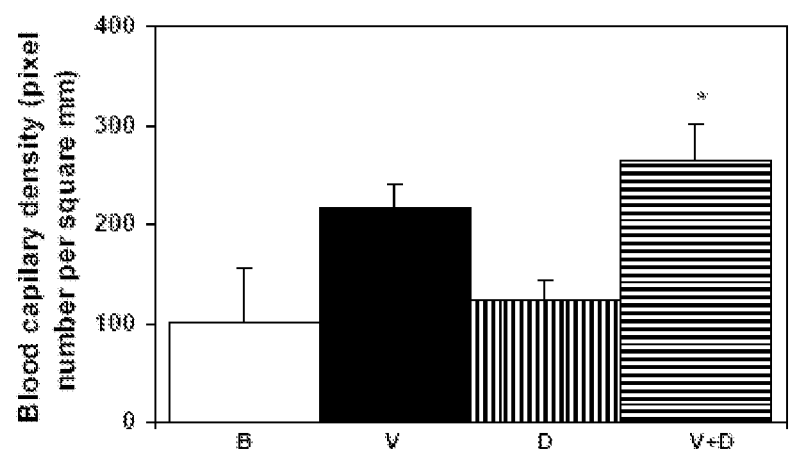
B
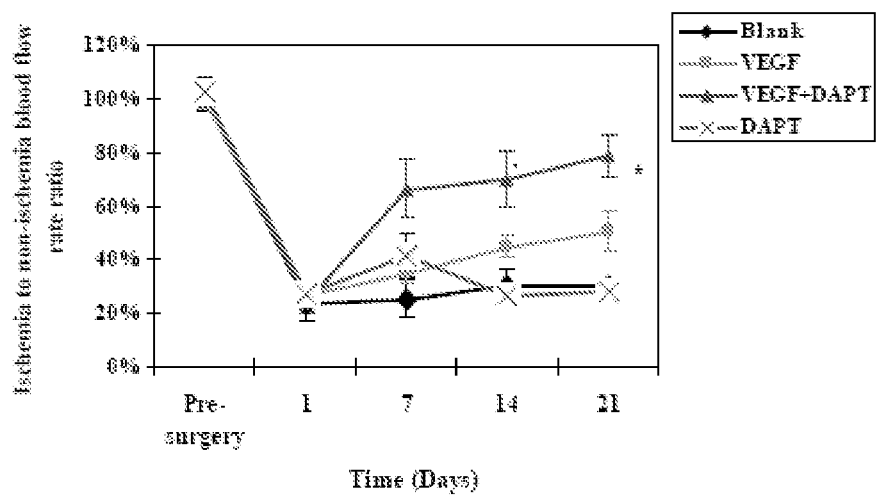

FIGURE 8
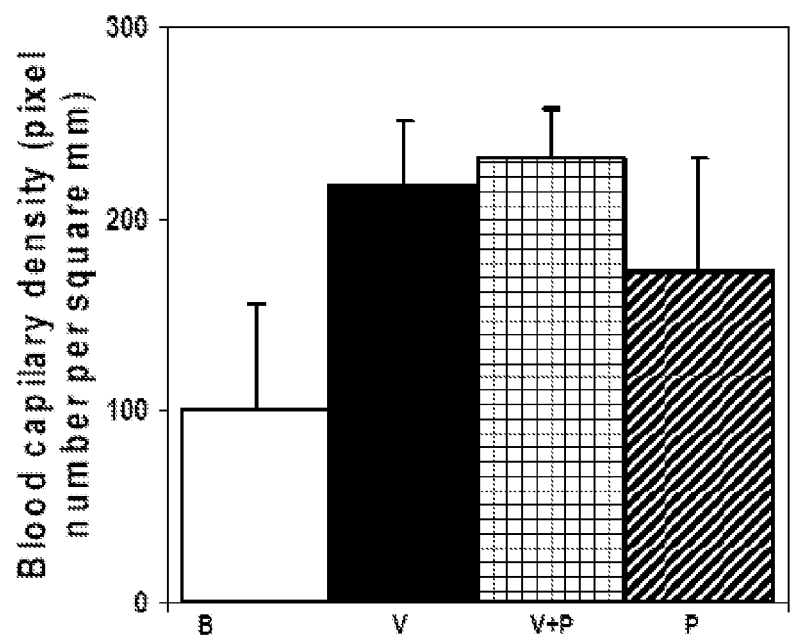
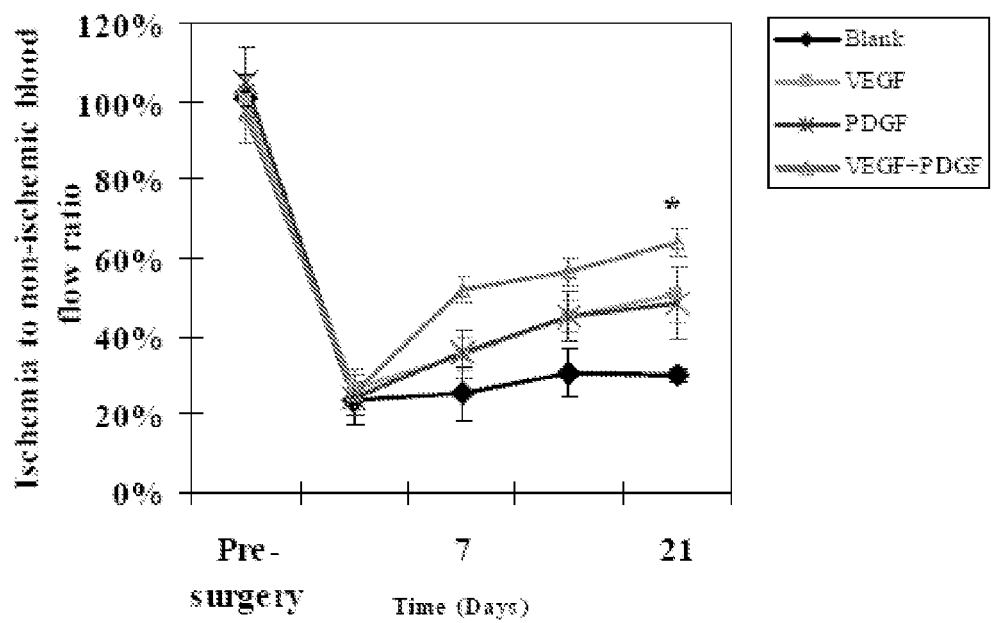

FIGURE 9
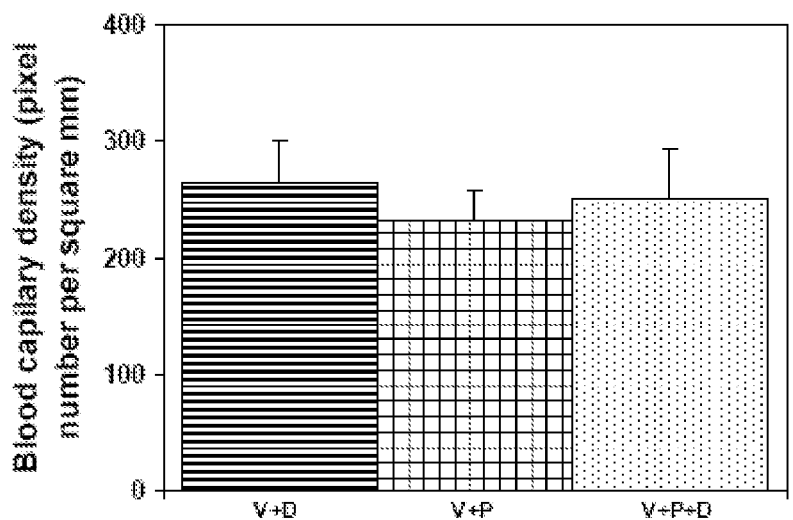
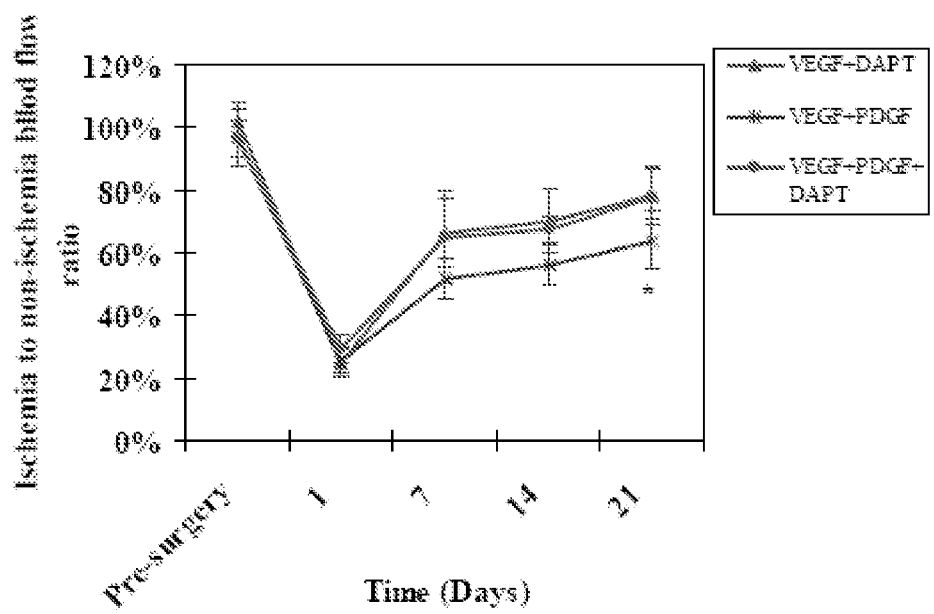

FIGURE 10
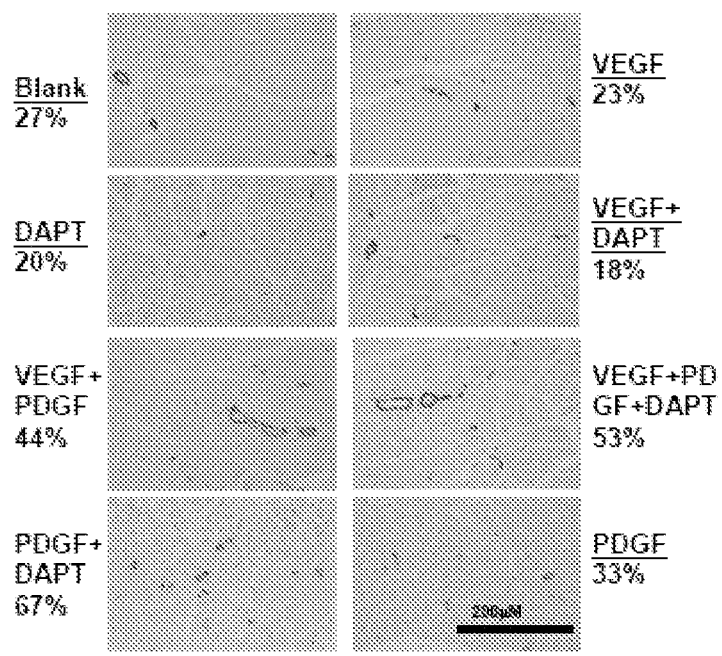
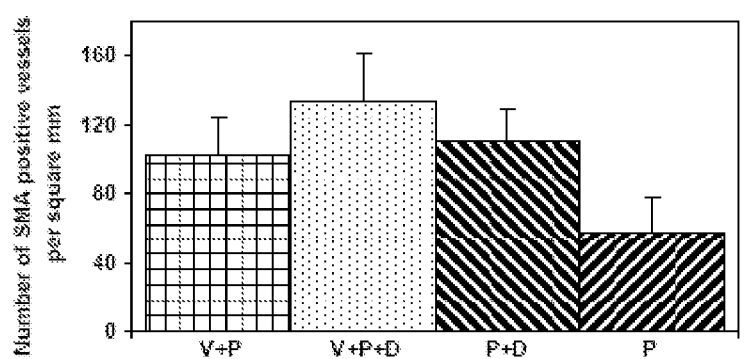

```
                       SEQUENCE LISTING

<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Gly Gly Gly Gly Arg Gly Asp Ser Pro
1               5

<210> SEQ ID NO 2
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Xaa Asx Asx Xaa Asx Xaa
1               5

<210> SEQ ID NO 3
<211> LENGTH: 6
<212> TYPE: PRT
<213> ORGANISM: Homo sapiens

<400> SEQUENCE: 3

Pro Arg Arg Ala Arg Val
1               5

<210> SEQ ID NO 4
<211> LENGTH: 19
<212> TYPE: PRT
<213> ORGANISM: Homo sapiens

<400> SEQUENCE: 4

Tyr Glu Lys Pro Gly Ser Pro Pro Arg Glu Val Val Pro Arg Pro Arg
1               5                   10                  15

Pro Gly Val
```

```
<210> SEQ ID NO 5
<211> LENGTH: 28
<212> TYPE: PRT
<213> ORGANISM: Homo sapiens

<400> SEQUENCE: 5

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 6
<211> LENGTH: 17
<212> TYPE: PRT
<213> ORGANISM: Homo sapiens

<400> SEQUENCE: 6

Arg Ile Gln Asn Leu Leu Lys Ile Thr Asn Leu Arg Ile Lys Phe Val
1               5                   10                  15

Lys

<210> SEQ ID NO 7
<211> LENGTH: 5
<212> TYPE: PRT
<213> ORGANISM: Homo sapiens

<400> SEQUENCE: 7

Leu Arg Gly Asp Asn
1               5

<210> SEQ ID NO 8
<211> LENGTH: 5
<212> TYPE: PRT
<213> ORGANISM: Homo sapiens

<400> SEQUENCE: 8

Ile Lys Val Ala Val
1               5

<210> SEQ ID NO 9
<211> LENGTH: 5
<212> TYPE: PRT
<213> ORGANISM: Homo sapiens

<400> SEQUENCE: 9

Tyr Ile Gly Ser Arg
1               5

<210> SEQ ID NO 10
<211> LENGTH: 5
<212> TYPE: PRT
<213> ORGANISM: Homo sapiens

<400> SEQUENCE: 10

Pro Asp Ser Gly Arg
1               5

<210> SEQ ID NO 11
<211> LENGTH: 10
<212> TYPE: PRT
<213> ORGANISM: Homo sapiens

<400> SEQUENCE: 11

Arg Asn Ile Ala Glu Ile Ile Lys Asp Ala
```

<210> SEQ ID NO 12
<211> LENGTH: 354
<212> TYPE: PRT
<213> ORGANISM: Homo sapiens

<400> SEQUENCE: 12

```
Met Thr Asp Arg Gln Thr Asp Thr Ala Pro Ser Pro Ser Tyr His Leu
 1               5                  10                  15
Leu Pro Gly Arg Arg Thr Val Asp Ala Ala Ser Arg Gly Gln
             20                  25                  30
Gly Pro Glu Pro Ala Pro Gly Gly Val Glu Gly Val Gly Ala Arg
             35                  40                  45
Gly Val Ala Leu Lys Leu Phe Val Gln Leu Leu Gly Cys Ser Arg Phe
 50                  55                  60
Gly Gly Ala Val Val Arg Ala Gly Glu Ala Glu Pro Ser Gly Ala Ala
 65                  70                  75                  80
Arg Ser Ala Ser Ser Gly Arg Glu Glu Pro Gln Pro Glu Glu Gly Glu
             85                  90                  95
Glu Glu Glu Glu Lys Glu Glu Glu Arg Gly Pro Gln Trp Arg Leu Gly
            100                 105                 110
Ala Arg Lys Pro Gly Ser Trp Thr Gly Glu Ala Ala Val Cys Ala Asp
            115                 120                 125
Ser Ala Pro Ala Ala Arg Ala Pro Gln Ala Leu Ala Arg Ala Ser Gly
130                 135                 140
Arg Gly Gly Arg Val Ala Arg Arg Gly Ala Glu Ser Gly Pro Pro
145                 150                 155                 160
His Ser Pro Ser Arg Arg Gly Ser Ala Ser Arg Ala Gly Pro Gly Arg
                165                 170                 175
Ala Ser Glu Thr Met Asn Phe Leu Leu Ser Trp Val His Trp Ser Leu
                180                 185                 190
Ala Leu Leu Leu Tyr Leu His His Ala Lys Trp Ser Gln Ala Ala Pro
            195                 200                 205
Met Ala Glu Gly Gly Gln Asn His His Glu Val Val Lys Phe Met
210                 215                 220
Asp Val Tyr Gln Arg Ser Tyr Cys His Pro Ile Glu Thr Leu Val Asp
225                 230                 235                 240
Ile Phe Gln Glu Tyr Pro Asp Glu Ile Glu Tyr Ile Phe Lys Pro Ser
                245                 250                 255
Cys Val Pro Leu Met Arg Cys Gly Gly Cys Cys Asn Asp Glu Gly Leu
                260                 265                 270
Glu Cys Val Pro Thr Glu Glu Ser Asn Ile Thr Met Gln Ile Met Arg
            275                 280                 285
Ile Lys Pro His Gln Gly Gln His Ile Gly Glu Met Ser Phe Leu Gln
            290                 295                 300
His Asn Lys Cys Glu Cys Arg Pro Lys Lys Asp Arg Ala Arg Gln Glu
305                 310                 315                 320
Asn Pro Cys Gly Pro Cys Ser Glu Arg Arg Lys His Leu Phe Val Gln
                325                 330                 335
Asp Pro Gln Thr Cys Lys Cys Ser Cys Lys Asn Thr Asp Ser Arg Cys
            340                 345                 350
Lys Met
```

<210> SEQ ID NO 13
<211> LENGTH: 371
<212> TYPE: PRT
<213> ORGANISM: Homo sapiens

<400> SEQUENCE: 13

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
                35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
    195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
    275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Cys Asp Lys
    355                 360                 365

Pro Arg Arg
    370
```

<210> SEQ ID NO 14
<211> LENGTH: 371
<212> TYPE: PRT
<213> ORGANISM: Homo sapiens

<400> SEQUENCE: 14

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Ser Leu Thr
        355                 360                 365

Arg Lys Asp
    370

```
<210> SEQ ID NO 15
<211> LENGTH: 389
<212> TYPE: PRT
<213> ORGANISM: Homo sapiens

<400> SEQUENCE: 15

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Pro Cys Gly Pro Cys Ser Glu Arg Lys His Leu Phe
            340                 345                 350

Val Gln Asp Pro Gln Thr Cys Lys Cys Ser Cys Lys Asn Thr Asp Ser
        355                 360                 365

Arg Cys Lys Ala Arg Gln Leu Glu Leu Asn Glu Arg Thr Cys Arg Cys
```

```
            370                 375                 380
Asp Lys Pro Arg Arg
385

<210> SEQ ID NO 16
<211> LENGTH: 395
<212> TYPE: PRT
<213> ORGANISM: Homo sapiens

<400> SEQUENCE: 16

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Pro Cys Gly Pro Cys Ser Glu
            340                 345                 350
```

```
Arg Arg Lys His Leu Phe Val Gln Asp Pro Gln Thr Cys Lys Cys Ser
            355                 360                 365

Cys Lys Asn Thr Asp Ser Arg Cys Lys Ala Arg Gln Leu Glu Leu Asn
    370                 375                 380

Glu Arg Thr Cys Arg Cys Asp Lys Pro Arg Arg
385                 390                 395

<210> SEQ ID NO 17
<211> LENGTH: 412
<212> TYPE: PRT
<213> ORGANISM: Homo sapiens

<400> SEQUENCE: 17

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Leu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335
```

```
Lys Ser Arg Tyr Lys Ser Trp Ser Val Tyr Val Gly Ala Arg Cys Cys
            340             345             350

Leu Met Pro Trp Ser Leu Pro Gly Pro His Pro Cys Gly Pro Cys Ser
        355             360             365

Glu Arg Arg Lys His Leu Phe Val Gln Asp Pro Gln Thr Cys Lys Cys
    370             375             380

Ser Cys Lys Asn Thr Asp Ser Arg Cys Lys Ala Arg Gln Leu Glu Leu
385             390             395             400

Asn Glu Arg Thr Cys Arg Cys Asp Lys Pro Arg Arg
                405             410

<210> SEQ ID NO 18
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 18

Gly Cys Arg Asp Gly Pro Gln Gly Ile Trp Gly Gln Asp Arg Cys Gly
1               5                   10                  15
```

CONTROLLED RELEASE OF GROWTH FACTORS AND SIGNALING MOLECULES FOR PROMOTING ANGIOGENESIS

RELATED APPLICATIONS

This application is a national stage application, filed under 35 U.S.C. §371, of International Application No. PCT/US2009/045856, filed Jun. 1, 2009, which claims the benefit of provisional application U.S. Ser. No. 61/130,486, filed May 30, 2008, the contents of which are incorporated by reference in their entireties.

GOVERNMENT SUPPORT

This invention was made with Government support under RO1 HL069957 awarded by the National Institutes of Health. The Government has certain rights in the invention.

FIELD OF THE INVENTION

The present invention relates to the fields of cardiology, tissue repair, and preventative medicine.

BACKGROUND OF THE INVENTION

Angiogenesis refers to a process of new blood vessel formation. Subjects suffering from coronary arterial disease (CAD) and peripheral arterial disease (PAD) can be treated by promoting angiogenesis in the tissue lacking sufficient blood flow. However, current methods of administering angiogenic drugs are sub-optimal because they cannot control the presentation of multiple compounds separately. Moreover, systemic administration of drugs at concentrations that are therapeutically effective for the affected area cause surrounding, healthy, tissues to be exposed unnecessarily to pro-angiogenic growth factors and could lead to undesirable side effects.

SUMMARY OF THE INVENTION

The present invention provides compositions and methods for controlling the local presentations of pro-angiogenic growth factors and signaling molecules that are together used to achieve angiogenesis at the tissue or organ of interest. The compositions and methods of the present invention allow the concerted and joint presentations of delivered growth factors and signaling molecules to be controlled separately by changing physical and/or chemical properties of the polymer delivery material to achieve an appropriate local concentration of the factor/molecules at the target tissue site.

Subjects to be treated in the manner described herein have been diagnosed as suffering from or at risk of developing an ischemic condition. The methods are suitable to treatment of human patients, as well as being suitable for veterinary use (e.g., treatment of companion animal such as dogs and cats. In a preferred embodiment, the methods are used to develop treatments for chronic ischemia in coronary and peripheral artery disease for diabetic subjects. Alternatively, or in addition, the present invention is used to improve wound healing in ulcers for diabetic subjects. The impaired endothelial tissues of diabetic subjects often have a reduced response to regular pro-angiogenic factors, making the continuous activation of vascular growth induced by the sustained and distinct presentation of growth factors and signaling molecules provided by the present invention particularly valuable. This type of continuous, sustained, and distinct presentation of pro-angiogenic factors and signaling molecules is not currently possible. Current methods that attempt to achieve similar therapeutic outcomes also induce deleterious side-effects due to substantial systemic dissemination of these factors throughout the body.

A device, which overcomes the shortcomings of existing approaches, comprises a scaffold composition, a bioactive composition, and a regulatory agent. The bioactive composition and the regulatory agent are incorporated into or coated onto the scaffold, e.g., a polymeric gel, composition, and the regulatory agent controls the activity of the bioactive agent. The bioactive composition is released from the scaffold composition at a first rate and the regulatory agent is released from said scaffold composition at a second rate. For example, the bioactive composition exits from the scaffold composition slower or faster relative to the regulatory agent. For example, vascular endothelial growth factor (VEGF) as a bioactive composition exits from the scaffold composition for a time period of one or more, e.g., 4 weeks, while gamma secretase inhibitor as a regulatory agent exits from the same scaffold composition for a time period of one or more days, e.g., 3 days. The difference between the release rates of multiple factors is important in determining the final angiogenesis outcomes. For example, the desired time-frame for Notch inhibitor delivery will be 7-20 fold (e.g., 8, 10, 15, or 18-fold) shorter than that of VEGF or PDGF, i.e., Notch inhibitor is released within 1-3 days while VEGF or PDGF is released within 7-60 days (e.g., 7, 10, 15, 30, 45, or 60 days). An exemplary bioactive composition is a pro-angiogenic factor such as VEGF and/or PDGF and an exemplary regulatory agent is an inhibitor or enhancer of angiogenesis such as DAPT.

One or more bioactive compositions are incorporated into or coated onto the scaffold composition, and the scaffold composition temporally controls release of the bioactive composition. Alternatively, or in addition, the scaffold composition spatially controls release of a bioactive composition. In another embodiment, the bioactive composition incorporated into or coated onto the scaffold composition temporally or spatially regulates release of a second bioactive composition.

The present invention also comprises a method of inducing blood vessel growth in a target tissue of a mammal, comprising providing a device comprising a scaffold composition with a bioactive composition being incorporated therein or thereon and contacting a mammalian tissue with the device wherein said scaffold composition temporally controls release of the bioactive composition and wherein the bioactive composition induces angiogenesis within the target tissue. For example, a polymeric gel composition loaded with pro-angiogenic factors and a regulatory factor is injected directly into the target site, or into a site that is adjacent to or in close proximity to the target site in which angiogenesis is desired. For example, the site of administration is 10 mm, 25 mm, 50 mm, 1 cm, 5 cm, 10 cm, 50 cm from the target tissue site where angiogenesis is to occur. In addition, multiple simultaneous injections (in different spatial locations, e.g., encircling or surrounding an affected anatomical location/site), or repeating injections every 1-2 weeks, at the same site or every few mm or cm apart in an ischemic region may be desirable.

The present invention further comprises a method of augmenting blood vessel growth, comprising providing a device comprising a scaffold composition with a bioactive composition being incorporated therein or thereon and contacting a mammalian tissue with the device, wherein said scaffold composition temporally controls release of the bioactive composition and wherein the bioactive composition induces growth from existing blood vessels.

The bioactive composition of the devices of the present invention is non-covalently linked to said scaffold composition. Alternatively, the bioactive composition is covalently linked to said scaffold composition.

Bioactive compositions of the present invention consist of, consist essentially of, or comprise one or more factors, which are administered either by direct protein delivery or delivering gene sequences to have cells locally make proteins. Exemplary bioactive compositions can include receptor ligands, transcription factors, and/or regulatory molecules.

Receptor ligands include, but are not limited to, vascular endothelial growth factor (VEGF (A-F)), fibroblast growth factors (acidic and basic FGF 1-10), granulocyte-macrophage colony-stimulating factor (GM-CSF), insulin, insulin growth factor or insulin-like growth factor (IGF), insulin growth factor binding protein (IGFBP), placenta growth factor (PIGF), angiopoietin (Ang1 and Ang2), platelet-derived growth factor (PDGF), hepatocyte growth factor (HGF), transforming growth factor (TGF-α, TGF-β, isoforms 1-3), platelet-endothelial cell adhesion molecule-1 (PECAM-1), vascular endothelial cadherin (VE-cadherin), nitric oxide (NO), chemokine (C-X-C motif) ligand 10 (CXCL10) or IP-10, interleukin-8 (IL-8), hypoxia inducible factor (HIF), monocyte chemotactic protein-1 (MCP-1), vascular cell adhesion molecule (VCAM), ephrin ligands (including Ephrin-B2 and -B4).

Transcription factors include, but are not limited to, HIF-1α, HIF-1β and HIF-2α, Ets-1, Hex, Vezf1, Hox, GATA, LKLF, COUP-TFII, Hox, MEF2, Braf, Prx-1, Prx-2, CRP2/SmLIM and GATA family members, basic helix-loop-helix factors and their inhibitors of differentiation.

Regulatory molecules include, but are not limited to, enzymes (matrix metalloproteinase (MMP), tissue plasminogen activator (PLAT or tPA), cyclooxygenase (COX), angiogenin), molecules regulating Notch signaling which consists of, consists essentially of, or comprises monoclonal antibodies to Notch ligands and receptors, RNA interference, antisense Notch, receptor and mastermind-like 1 (MAML1) decoys, beta and gamma-secretase inhibitors (GSI), or any other molecules that can activate or inhibit Notch signaling.

Devices of the present invention consist of, consist essentially of, or comprise one or more bioactive compositions. A second bioactive composition consists of, consists essentially of, or comprises a signaling molecule selected from the group consisting of monoclonal antibodies to Notch ligands and receptors, RNA interference, antisense Notch, receptor and mastermind-like 1 (MAML1) decoys, beta and gamma-secretase inhibitors (GSI), or any other molecules that can activate or inhibit Notch signaling.

Alternatively, or in addition, signaling molecules of the second bioactive composition are selected from the group of any other molecules that can inhibit or activate Notch signaling. In a preferred embodiment of the present invention, the signaling molecule is DAPT (N—[N-(3,5-Difluorophenacetyl-L-alanyl)]-S-phenylglycine t-butyl ester) (Sigma-Aldrich, St. Louis, Mo.). Signaling molecules of the second bioactive composition are released from scaffolds and devices simultaneously or sequentially with each other. Signaling molecules of the second bioactive composition are released from scaffolds and devices simultaneously or sequentially with bioactive compositions comprising angiogenic factors. Preferably, the regulatory molecule is a Notch inhibitor such as the gamma secretase inhibitor DAPT.

Scaffold compositions of the present invention degrade at a predetermined rate based on a physical parameter selected from the group consisting of temperature, pH, hydration status, and porosity. Alternatively, or in addition, scaffold compositions are enzymatically digested by a composition elicited by a contacting cell, said release of said bioactive composition being dependent upon the rate of enzymatic digestion. A contacting cell is defined as a cell belonging to a target cell wherein the scaffold composition or device resides that physically contacts or adheres to the scaffold composition or device.

Scaffold compositions of the present invention contain an external surface. Alternatively, or in addition, scaffold compositions contain an internal surface. External or internal surfaces of the scaffold composition are solid or porous. Pore size is less than about 10 nm, in the range of about 10 nm-20 μm in diameter, or greater than about 20 μm. A scaffold composition with multiple internal surfaces optionally comprises one or more compartments.

Devices of the present invention are administered by intramuscular injection. Alternatively, or in addition, scaffold compositions and devices are administered by intraperitoneal injection, or endoscopic delivery or other minimally invasive delivery approach, or surgically implanted. Preferably, the loaded gel composition is injected as a bolus using a standard syringe and injection needle at or near the target angiogenesis site, or it can be surgically implanted or delivered via a catheter.

The devices and methods of the invention provide a solution to several problems associated with previous angiogenesis-inducing protocols. The bioactive composition is incorporated into or coated onto the scaffold composition. The scaffold composition and/or bioactive composition temporally and spatially (directionally) controls release of one or more additional bioactive compositions.

This device includes a scaffold composition which incorporates into or is coated with a bioactive composition; the device releases one or more bioactive compositions comprised of pro-angiogenic factors and signaling molecules to stimulate local vascular growth. Release of the bioactive composition is regulated spatially and temporally. Depending on the application for which the device is designed, the device regulates release through the physical or chemical characteristics of the scaffold itself. For example, the scaffold composition is differentially permeable, allowing release only in certain physical areas of the scaffold. The permeability of the scaffold composition is regulated, for example, by selecting or engineering a material for greater or smaller pore size, density, polymer cross-linking, stiffness, toughness, ductility, or viscoelascticity.

The scaffold composition contains physical channels or paths through which bioactive compositions can move more easily towards a targeted area of release of the device or of a compartment within the device. The scaffold composition is optionally organized into compartments or layers, each with a different permeability, so that the time required for a bioactive composition to move through the device is precisely and predictably controlled. Release is also regulated by the degradation, de- or re-hydration, oxygenation, chemical or pH alteration, or ongoing self-assembly of the scaffold composition. These processes are driven by diffusion or catalyzed by enzymes or other reactive chemicals.

Alternatively, or in addition, release is regulated by a bioactive composition. By varying the concentration of extracellular matrix components, adhesion molecules and other bioactive compounds in different areas of the device, including agents with means to create pores and enzymatically digest the scaffold composition, the bioactive composition has means to control the rate at which other elements of the same bioactive composition or additional bioactive compositions escape, or are released from the scaffold composition or device. The device controls and directs the flow of bioactive compositions or elements through its structure.

Chemical affinities are used to channel bioactive compositions towards a specific area of release. By varying the density and mixture of those bioactive substances, the device controls the timing of the combination and release of elements of bioactive compositions or multiple bioactive compositions. In one embodiment, components of a bioactive composition or two compositions are separated initially, but combined when allowed to flow through channels in the scaffold composition towards an area of release. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by neighboring cells.

Cells in close physical proximity to the scaffold compositions and devices of the present invention, or those in physical contact with the scaffold composition and devices, secrete enzymes that affect the one or more features of the scaffold composition. Neighboring or juxtaposed cells residing within target tissues increase or decrease the structural integrity of the scaffold composition through directly (e.g., release of enzymes) or indirectly (e.g. release of signals recruiting cells to the scaffold compositions that affect structural integrity). Neighboring or juxtaposed cells produce factors that increase or decrease the rigidity, increase or decrease the porosity, increase or decrease the potential for or rate of degradation, increase or decrease the adhesion or mobility, or increase or decrease the immunogenicity of the scaffold composition or device. Alternatively, the scaffold composition is comprised of materials that are unaffected by enzymatic activity and are unaffected by cellular secretions from local tissues.

The physical or chemical structure of the scaffold also regulates the diffusion of bioactive agents through the device. The release profiles of multiple bioactive compositions are made distinct from each other by adjusting the properties and formulation of delivery vehicle. For example, the small-molecule-weight signaling molecule is first incorporated into microspheres followed by incorporation into alginate hydrogel, so that the signaling molecules have a more delayed release compared to the growth factors. The pore size, oxidization degree, molecular weight distribution of the alginate gel are varied to control the release rate of incorporated growth factors.

The bioactive composition includes one or more compounds that regulate cell function and/or behavior. The bioactive composition is covalently linked to the scaffold composition or non-covalently associated with the scaffold. For example, the bioactive composition is an extracellular matrix (ECM) component that is chemically crosslinked to the scaffold composition. Regardless of the tissue of origin, ECM components generally include three general classes of macromolecules: collagens, proteoglycans/glycosaminoglycans (PG/GAG), and glycoproteins, e.g., fibronectin (FN), laminin, and thrombospondin. ECM components associate with molecules on the cell surface and mediate adhesion and/or motility. Preferably, the ECM component associated with the scaffold is a proteoglycan attachment peptide or cyclic peptide containing the amino acid sequence arginine-glycine-aspartic acid (RGD). Proteoglycan attachment peptides are selected from the group consisting of $G_4$RGDSP (SEQ ID NO: 1), XBBXBX (SEQ ID NO: 2), PRRARV (SEQ ID NO: 3), YEKPGSPPREVVPRPRPGV (SEQ ID NO: 4), RPSLAKKQRFRHRNRKGYRSQRGHSRGR (SEQ ID NO: 5), and RIQNLLKITNLRIKFVK (SEQ ID NO: 6), and cell attachment peptides are selected from the group consisting of RGD, RGDS, LDV, REDV, RGDV, LRGDN (SEQ ID NO: 7), IKVAV (SEQ ID NO: 8), YIGSR (SEQ ID NO: 9), PDSGR (SEQ ID NO: 10), RNIAEIIKDA (SEQ ID NO: 11), RGDT, DGEA, and VTXG.

Components of the ECM, e.g., FN, laminin, and collagen, interact with the cell surface via the integrin family of receptors, a group of divalent cation-dependent cell surface glycoproteins that mediate cellular recognition and adhesion to components of the ECM and to other cells. Ligands recognized by integrins typically contain an RGD amino acid sequence that is expressed in many ECM proteins. Exemplary molecules that mediate cell adhesion and/or movement include FN, laminin, collagen, thrombospondin 1, vitronectin, elastin, tenascin, aggrecan, agrin, bone sialoprotein, cartilage matrix protein, fibrinogen, fibrin, fibulin, mucins, entactin, osteopontin, plasminogen, restrictin, serglycin, SPARC/osteonectin, versican, von Willebrand Factor, polysaccharide heparin sulfate, cell adhesion molecules including connexins, selectins include collagen, RGD (Arg-Gly-Asp) and YIGSR (Tyr-Ile-Gly-Ser-Arg) peptides, glycosaminoglycans (GAGs), hyaluronic acid (HA), integrins, selectins, cadherins and members of the immunoglobulin superfamily. Carbohydrate ligands of the ECM include the polysaccharides hyaluronic acid, and chondroitin-6-sulfate.

The device optionally contains a second or third bioactive composition(s), e.g., a growth factor, differentiation factor, or signaling molecule. For example, the device includes vascular endothelial growth factor (VEGF), hepatocyte growth factor (HGF), or fibroblast growth factor 2 (FGF2) or a combination thereof. Growth factors used to promote angiogenesis, wound healing, and other aspects of tissue regeneration are listed herein and are used alone or in combination to induce regeneration of bodily tissues by bioactive compositions released from an implanted scaffold device.

The bioactive composition(s) described above is non-covalently linked to the scaffold composition. Alternatively, or in addition, the bioactive composition is covalently associated with the scaffold. Noncovalent bonds are generally one to three orders of magnitude weaker than covalent bonds permitting diffusion of the factor out of the scaffold and into surrounding tissues. Noncovalent bonds include electrostatic, hydrogen, van der Waals, π aromatic, and hydrophobic. For example, a growth factor such as VEGF is associated with the device by noncovalent bonds and exits the device following administration of the device to a target site to promote angiogenesis within the target bodily tissue.

The polymer scaffold composition into or onto which the bioactive composition (growth factor, and/or regulatory molecule are loaded is biocompatible. The composition is biodegradable/erodable or resistant to breakdown in the body. Relatively permanent (degradation resistant) scaffold compositions include metals and some polymers such as silk. Preferably, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks. A typical volume of alginate gel is 1 μL to 1 mL, with a degradation time ranging from 1 day to 6 weeks.

In one example, cells mediate degradation of the scaffold matrix, i.e., the scaffold composition is enzymatically digested by a composition elicited by a neighboring cell, and the release of the bioactive composition is dependent upon the rate of enzymatic digestion of the scaffold. In this case, polymer main chains or cross-links contain compositions, e.g., oligopeptides, which are substrates for collagenase or plasmin, or other enzymes produced by cells adjacent to the scaffold.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above. One preferred scaffold composition includes alginate gels.

Porosity of the scaffold composition influences release of one or more bioactive compositions from the device. Pores are nanoporous, microporous, or macroporous. For example, the diameter of nanopores are less than about 10 nm; micropore are in the range of about 100 nm-20 μm in diameter; and, macropores are greater than about 20 μm (preferably greater than about 100 μm and even more preferably greater than about 400 μm). In one example, the scaffold is macroporous with aligned pores of about 400-500 μm in diameter.

In one preferred embodiment of the invention, one or more of the bioactive compositions contains an element with means to chemically induce pores in the scaffold composition that are nanoporous, microporous, or macroporous in size. The abundance of this element and the presence or absence of other elements that augment or inhibit the activity of this pore-making element determine pore size and density, and consequently, the rate at which one or more bioactive compositions passively escape or are actively released from the scaffold composition. Exemplary elements with means to chemically induce pores in the scaffold composition include, but are not limited to, potassium salts, calcium salts, magnesium salts, amino acids, week acids, carbohydrates, potassium bitartrate, creatine, aspargine, glutamine, aspartic acid, glutamic acid, leucin, neroleucine, inosine, isoleucine, magnesium citrate, magnesium phosphate, magnesium carbonate, magnesium hydroxide, and magnesium oxide. Pore-forming elements are also enzymes incorporated into or coated onto the scaffold composition. One or more of these elements are initially contained within separate compartments of the scaffold composition and later combined by having one or more of these elements flow through common channels or paths in the scaffold composition. These elements individually have means to induce pore formation in the scaffold composition. Alternatively, these elements are combined, and the resulting combination has means to induce pore formation in the scaffold composition.

The devices are manufactured in their entirety in the absence of cells or can be assembled around or in contact with cells (the material is gelled or assembled around cells in vitro or in vivo in the presence of cells and tissues). In one embodiment of the invention, the scaffold composition material with one or more bioactive compositions incorporated, is injected into a target tissue where local blood flow is restricted or would healing is impaired.

The device is manufactured in one stage comprising one layer or compartment. Alternatively, the device is manufactured in two or more (3, 4, 5, 6, . . . 10 or more) stages in which one layer or compartment is made and infused or coated with a bioactive composition followed by the construction of a second, third, fourth or more layers, which are in turn infused or coated with a bioactive composition in sequence. Each layer or compartment is identical to the others or distinguished from one another by the elements comprising the bioactive composition incorporated into or coated onto them as well as distinct chemical, physical and biological properties.

A method of making a scaffold is carried out by providing a scaffold composition and covalently linking or noncovalently associating the scaffold composition with a first bioactive composition. The scaffold composition is also contacted with a second bioactive composition. The second bioactive composition is non-covalently associated with the scaffold composition to yield a doped (loaded) scaffold, i.e., a scaffold composition that includes one or more bioactive substances. The contacting steps are optionally repeated to yield a plurality of doped scaffolds, e.g., each of the contacting steps is characterized by a different amount of the second bioactive composition to yield a gradient of the second bioactive composition in the scaffold device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The method optionally involves adhering individual niches, layers, or components to one another and/or insertion of semi-permeable, permeable, or nonpermeable membranes within or at one or more boundaries of the device to further control/regulate locomotion of cells or bioactive compositions.

Therapeutic applications of the device include vascular tissue generation, regeneration and repair. A mammalian tissue is contacted with the device. The scaffold composition and/or the bioactive composition spatially or directionally regulates release of a bioactive composition with means to promote angiogenesis in local tissues such as vascular, muscle, gastrointestinal, e.g., bowel, cardiac, brain, kidney, bone, nerve both central and peripheral nervous system (CNS and PNS) or any tissue characterized by a shortage of oxygen or nutrients or in which the vasculature is damaged, absent, or functionally impaired.

A method of inducing local angiogenesis in a target tissue is carried out by administering to a mammal a device containing a scaffold composition and a bioactive composition incorporated therein or thereon. The scaffold composition and/or bioactive composition induces release of pro-angiogenic factors and signaling molecules from the device into the local tissue environment. The release of these angiogenic factors is controlled spatially and temporally. Release can be sustained at a steady rate/dosage for a desired period of time, e.g., minutes; 0.2. 0.5, 1, 2, 4, 6, 12, 24 hours; 2, 4, 6, days; weeks (1-4), months (2, 4, 6, 8, 10, 12) or years, during which the cells are exposed to structural elements and bioactive compositions that lead to improved vascular growth.

Other features and advantages of the invention will be apparent from the following description of the preferred embodiments thereof, and from the claims. All references cited herein are incorporated by reference.

BRIEF DESCRIPTION OF THE DRAWINGS

FIGS. 5A-B are bar graphs showing the effect of VEGF and DAPT on blood capillary density. An in vivo model was used to test the effect of controlled presentation of VEGF and DAPT on newly formed blood vessel density in an ischemia situation. +: use of the substance. –: lack of the substance. gel: alginate gel. im: intramuscular injection. ip: intraperitoneal injection.

FIG. 7A is a bar graph showing the effect of VEGF, DAPT, and the combination on blood capillary density.

FIG. 7B is a line graph showing the effect of VEGF, DAPT, and the combination on blood flow.

FIG. 8A is a bar graph showing the effect of VEGF, PDGF, and the combination on blood capillary density.

FIG. 8B is a line graph showing the effect of VEGF, PDGF, and the combination on blood flow.

FIG. 9A is a bar graph showing the effect of VEGF, DAPT, PDGF, and combinations thereof on blood capillary density.

FIG. 9B is a line graph showing the effect of VEGF, DAPT, PDGF, and combinations thereof on blood flow.

DETAILED DESCRIPTION OF THE INVENTION

Figure 1:
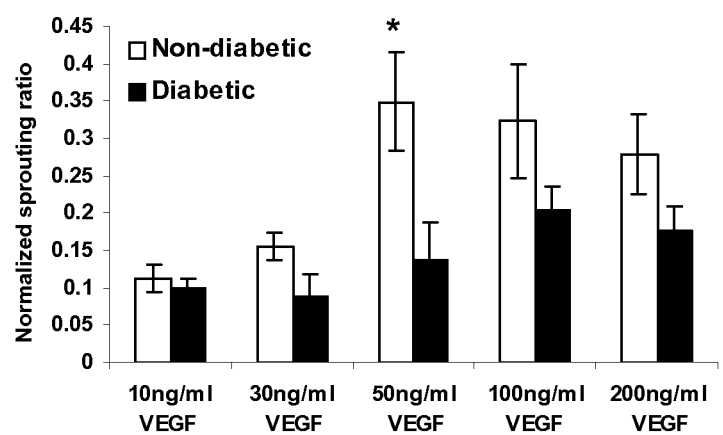
FIG. 1 is a bar graph showing the effect of VEGF on sprouting ratio. An in vitro model was used to test the significance of a controlled local concentration of VEGF.

The use of compounds that can modulate the signaling of growth factors, e.g., gamma-secretase inhibitors (GSI), to promote angiogenesis, has been proposed (US 2006/0264380 A1). However, these previous studies did not indicate a need to provide the compounds over particular time-frames, nor do they provide any method to achieve a sustained presence of the compounds. Previous studies mention the use of a combination of pro-angiogenic factors together with GSI. Functionally, a bolus injection of multiple pro-angiogenesis compounds simultaneously cannot control the presentation of each individual compound separately, as they may each need to have a distinct presentation. More importantly, single or multiple injections that introduce drugs into system circulation represent a sub-optimal method to reach the therapeutic level at the specific tissue of interest, and can result in high concentrations of drug accumulation at distant organs or tissues, which may lead to various side effects.

The current invention provides a method to control the local presentations of pro-angiogenic growth factors and signaling molecules that are together used to achieve angiogenesis at the tissue or organ of interest. The spatial and temporal presentation of delivered growth factors and signaling molecules can be controlled separately by fine-tuning the physical and chemical properties of the polymer delivery material.

Specifically, this invention will be especially useful for developing treatments for chronic ischemia in coronary or peripheral artery disease for diabetics, or wound healing in diabetes ulcers, as the impaired endothelium in these patients normally have a reduced response to regular pro-angiogenesis factors, thus a continuous activation by the sustained and distinct presentation of growth factors and signaling molecules may be critical. This is currently not achievable by other methods without inducing possible side-effects.

Angiogenesis refers to a process of new blood vessel formation. Patients suffering from coronary arterial disease (CAD) and peripheral arterial disease (PAD) can be treated by promoting angiogenesis in the tissue lacking sufficient blood blow. To deliver compounds to induce angiogenesis is therefore a promising therapeutic approach. Many growth factors, (e.g. vascular endothelial growth factor (VEGF), play a vital role in inducing angiogenesis by mediating the proliferation, migration and differentiation of endothelial cells. Molecules that can modulate the signaling pathways of growth factors, such as Notch inhibitors (e.g., gamma secretase inhibitors (GSI)), can also be used to augment the angiogenesis process. Therefore, delivering growth factors together with molecules mediating signaling pathways may have a beneficial effect.

Current delivery approaches mainly rely on injection of factors/molecules alone, i.e., in the absence of a scaffold composition. However, single injection is insufficient for circumstances where growth factors and signaling molecules need to be present over long time-frames, as they both have a short half-life. In addition, bolus injection of multiple compounds simultaneously cannot control the existence of each individual compound separately, if they each need to have a distinct presentation. More importantly, single or multiple injections that introduce drugs into system circulation are sub-optimal to reach the therapeutic level at the specific tissue of interest, and can result in high concentrations at distant organs or tissues, which may lead to various side effects.

The current invention utilizes an injectable biocompatible polymer material system incorporating pro-angiogenic growth factors, together with molecules that modulate the signaling pathway, to achieve angiogenesis at the tissue or organ of interest. The spatial and temporal presentation of delivered growth factor and signaling molecules can be controlled separately by fine-tuning the physical and chemical properties of the polymer material.

Angiogenesis

Angiogenesis is a physiological process wherein new blood vessels arise or extend from pre-existing vessels. The present invention encompasses methods of promoting blood vessel growth from existing vessels, as well as spontaneous blood vessel growth (also referred to as vasculogenesis) and arteriogenesis (collateral vessel formation). The term "angiogenesis" is meant to encompass all three methods of blood vessel formation named supra.

Angiogenesis is a normal process in growth and development, as well as in wound healing. Compositions and methods of the present invention induce or augment endogenous mechanisms for regulating angiogenesis and/or wound healing. Alternatively, or in addition, compositions and methods of the present invention introduce exogenous mechanisms for inducing or regulating angiogenesis and/or wound healing that do not normally occur in a target tissue. Furthermore, compositions and methods of the present invention induce, regulate, augment, or replace mechanisms for inducing or regulating angiogenesis and/or wound healing that are insufficient, aberrant, or incomplete compared to the endogenous mechanism due to genetic mutation, disease, infection, drug treatment, medical condition, or tissue transplant procedure.

Angiogenesis is also a fundamental step in the transition of neoplastic tumors from a dormant, or benign, state to a malignant, cancerous, or metastatic, state. Compositions and methods of the present invention disperse angiogenic factors and signaling molecules within a local tissue environment and do not allow for systemic administration or diffusion of bioactive compositions. This ability of the devices of the present invention to contain angiogenic factors to a confined target region demonstrates a significant clinical advantage over previous methods of delivery that are systemic in nature.

Controlled Release of Factors to Promote Angiogenesis

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective angiogenesis by the device is desired.

In the current system, the degradation rate of alginate, the polymer carrier, is controlled by its composition (for example, content of guluronic acid of alginate molecules, differential molecular weight distribution of alginate), physical and chemical treatment (e.g., irradiation or oxidization), and the degree of crosslinking which is controlled by the choice and the amount of the crosslinking agents (for e.g., ionic crosslinker or covalent crosslinker). More specifically, increasing the content of guluronic acid of alginate molecules will increase cross-linking and slow degradation, decreasing molecular weight will speed up degradation, irradiation will decrease molecular weight and thus increase the degradation rate, oxidization will increase the degradation rate, increasing the amount of crosslinker will slow the degradation rate, and different crosslinker molecules may result in differential crosslinking degree and affect the degradation rate.

The doses of the factors loaded in the alginate carrier are altered to achieve effective doses at a desired tissue site, e.g., from 1 to 10 microgram for $VEGF_{165}$, 1 to 10 microgram for PDGF-BB (dimeric glycoprotein composed of two B (-BB) chains), and 0.01 to 1 microgram for DAPT, for a mouse with an average weight of 10-50 g. An effective dosage amount or ratio of amounts is one that induces and promotes angiogenesis at the target tissue or organ site. The optimal dose is 3 to 10 microgram for $VEGF_{165}$, 3 to 10 microgram for PDGF-BB, 0.05 to 1 microgram for DAPT in the presence of VEGF at a dose of 1 to 10 microgram, and 0.05 to 1 microgram for DAPT in the presence of PDGF-BB at a dose of 1 to 10 microgram, for a mouse with an average weight of 10-50 g. The amounts and ratio of amounts scale up proportionately for humans.

The relative ratio of VEGF, PDGF and the Notch signaling molecule (e.g., DAPT) is critical in determining the final outcomes of angiogenesis. There exists an effective range and optimal value of the relative ratio between the amount of VEGF and DAPT, the amount of PDGF and DAPT, and the amount of VEGF, PDGF and DAPT. The effective range of the relative ratio (by mole) is 1:1 to 1:200 for $VEGF_{165}$ to DAPT, 1:1 to 1:200 for PDGF-BB to DAPT, and 1:0.1:1 to 1:10:200 for $VEGF_{165}$, PDGF-BB and DAPT, in the alginate polymer system. The optimal relative ratio (by mole) is 1:31 for $VEGF_{165}$ to DAPT, 1.8:31 for PDGF to DAPT, and 1:1.8:31 for $VEGF_{165}$:PDGF-BB:DAPT. The optimal ratio may vary depending on the specific delivery systems to be used, the species model (e.g., rat, rabbit, pig, dog, human and etc), and any change of the composition and the release kinetics of each of these factors.

Arteriosclerosis

Arteriosclerosis, or arterial disease, is a general term used to describe the thickening and hardening of the arteries. One particular kind of arteriosclerosis that contributes to heart disease is atherosclerosis. Atherosclerosis is a progressive disease that is characterized by a buildup of plaque within the arteries that may partially, or totally, block blood flow through an artery. Plaque is formed from fatty substances, cholesterol, cellular waste, calcium, and fibrin. Atherosclerosis generally results in ischemia, or restriction of the blood supply, for the tissues supplied by the blood carried in the blocked artery.

Oxygen Supply and Deprivation

Because oxygen is mainly bound to hemoglobin in red blood cells, insufficient blood supply causes tissue to become hypoxic, or, in more severe situations, when no oxygen is supplied, anoxic. Oxygen deprivation can cause necrosis, or cell death. In very aerobic tissues such as heart and brain, at body temperature, necrosis due to ischemia becomes irreversible in 3-4 hours. Complete oxygen deprivation to organs such as the heart and brain for greater than 20 minutes causes irreversible damage.

Ischemia is a consequence of heart diseases, transient ischemic attacks, cerebrovascular accidents, ruptured arteriovenous malformations, and peripheral artery occlusive disease. The heart, kidneys, and brain are the most sensitive organs to inadequate blood supply. Stroke, aneurism, hemorrhage, and traumatic injury of the brain commonly result in ischemic conditions. Ischemia in brain tissue induces the ischemic cascade, in which proteolytic enzymes, reactive oxygen species, and other harmful chemicals damage and may ultimately kill brain tissue. Similarly, artery disease and blockages can occlude blood flow to the heart inducing ischemia and death of heart muscle tissue. A macroscopic region of necrotic cells is called an infarction. Heart attacks lead to significant cell death from prolonged oxygen deprivation, also referred to as myocardial infarction.

Restoration of blood flow after a period of ischemia may cause more damage than the ischemia. Reintroduction of oxygen causes a greater production of damaging free radicals, resulting in reperfusion injury and accelerated necrosis.

Coronary Arterial Disease

Patients diagnosed with Coronary Arterial Disease (CAD, also called coronary heart disease, coronary artery disease, ischaemic heart disease, and atherosclerotic heart disease) results from the accumulation of atheromatous plaques within the walls of the arteries that supply the myocardium (heart muscle) with oxygen and nutrients. CAD encompasses a wide spectrum of patients with varying disease severity and prognosis. Patients with mild CAD and the best prognoses are asymptomatic. Mild CAD individuals have atheromatous streaks within the walls of their coronary arteries that do not obstruct blood flow and the lumen of their coronary artery is normal in calibre (as assessed by coronary angiogram). As an individual progresses along this spectrum toward more severe phenotypes, the atheromatous streaks along the coronary walls increase in thickness. Atheromatous plaques begin to form initially and expand into the walls of the artery but, ultimately, expand into the luman of the vessel where they will begin to restrict blood flow.

Once the plaques obstruct more than 70% of the diameter of the vessel lumen, the individual develops symptoms of obstructive coronary artery disease and is diagnosed with ischemic heart disease. The first symptoms of ischemic heart disease are often exertional angina (chest pain) or decreased exercise tolerance. Angina that occurs regularly with activity, upon awakening, or at other predictable times is termed stable angina. Angina that changes in intensity, character or frequency is termed unstable. Unstable angina may precede myocardial infarction.

The degree of severity of CAD can progress to near-complete or complete blockage of the coronary artery. At this end of the spectrum, most individuals experience one or more heart attacks (myocardial infarctions) and all experience chronic ischemia. If the blood flow to the heart tissue is restored to any degree, ischemic tissue is capable of a partial or full recovery depending upon the degree of blood flow restoration. Tissue that has suffered from an infarction is dead, and the damage is irreversible.

Peripheral Arterial Disease

Peripheral Arterial Disease (PAD, also called peripheral artery occlusive disease (PAOD), peripheral vascular disease, and peripheral artery disease) is caused by the obstruction of large peripheral arteries, which can result from atherosclerosis or inflammatory processes and can lead to a narrowing of the artery (stenosis) or obstruction of the artery by thrombus (obstruction by blood clot) or embolism (obstruction by object carried in blood stream from alternate location). PAD/PAOD results in ischemia that is either acute (rapid onset, short duration) or chronic (long-term). Exemplary symptoms of PAD/PAOD include, but are not limited to, claudication (pain, weakness, or cramping in muscles due to decreased blood flow); sores, wounds, or ulcers that heal slowly or incompletely; change in color (blueness, paleness) or cooling compared to other limbs; diminished hair or nail growth on affected limbs compared to unaffected limbs.

PAD/PAOD occurrence is often associated with or caused by smoking, diabetes mellitus, dyslipidemia (e.g. elevated cholesterol, including total cholesterol, LDL cholesterol, and triglyceride levels), hypertension, increased or decreased levels of inflammatory mediators (for example, C-reactive protein, homocysteine, and fibrinogen), aging (especially individuals over 50), racial background (especially prevalent among African-American individuals), gender (more frequently seen in males), obesity, or individuals with personal histories of vascular disease, heart attack, or stroke. The present invention encompasses methods of administering compositions, scaffolds, and devices to all individuals listed supra, for the purposes of repairing or replenishing blood supply to blood- and oxygen-deprived tissues.

PAD/PAOD is diagnosed using a number of tests. The initial test is an ankle brachial pressure index (ABPI/ABI) which measures the fall in blood pressure in the arteries supplying the legs. A reduced ABPI, quantitatively, a score of less than 0.9, suggests a diagnosis of PAD/PAOD. Moderate PAD/PAOD is diagnosed with a reduced ABPI score of less than 0.8. Severe PAD/PAOD is diagnosed with a reduced ABPI score of less than 0.5. However, conditions other than PAD/PAOD can result in reduced ABPI scores of less than 0.9. Thus, additional tests are performed to confirm a diagnosis of PAD/PAOD. A secondary examination usually comprises a lower limb Doppler ultrasound examination of the femoral artery. Alternatively, or in addition, imaging examinations can be performed by angiography using art-recognized standard methods. Furthermore, a multi-slice computerized tomography (CT) scan is used to directly image the arterial system.

PAD/PAOD severity is divided in the Fontaine stages (Fontaine R, Kim M, Kieny R (1954). Helvetica Chirurgica Acta, Basel 21 (5/6):499-533): mild pain while walking ("claudication")(stage I); severe pain on walking relatively shorter distances (intermittent claudication)(stage II); pain while resting (stage III); loss of sensation to the lower part of the extremity (stage IV); tissue loss (gangrene)(stage V).

Angiogenic Bioactive Compositions

Compositions and methods of the present invention comprise growth factors and signaling molecules that induce, regulate, or augment angiogenesis. Bioactive compositions of the present invention comprise one or more growth factors or signaling molecules incorporated into or coated onto the scaffold composition. Exemplary growth factors and signaling molecules encompassed by the present invention include, but are not limited to, vascular endothelial growth factor (VEGF (A-F)), fibroblast growth factors (acidic and basic FGF 1-10), granulocyte-macrophage colony-stimulating factor (GM-CSF), insulin, insulin growth factor or insulin-like growth factor (IGF), insulin growth factor binding protein (IGFBP), placenta growth factor (PIGF), angiopoietin (Ang1 and Ang2), platelet-derived growth factor (PDGF), hepatocyte growth factor (HGF), transforming growth factor (TGF-$\alpha$, TGF-$\beta$, isoforms 1-3), platelet-endothelial cell adhesion molecule-1 (PECAM-1), vascular endothelial cadherin (VE-cadherin), nitric oxide (NO), chemokine (C-X-C motif) ligand 10 (CXCL10) or IP-10, interleukin-8 (IL-8), hypoxia inducible factor (HIF), monocyte chemotactic protein (MCP), vascular cell adhesion molecule (VCAM), ephrin ligands (including Ephrin-B2 and -B4); Transcription factors such as HIF-1$\alpha$, HIF-10 and HIF-2$\alpha$, Ets-1, Hex, Vezf1, Hox, GATA, LKLF, COUP-TFII, Hox, MEF2, Braf, Prx-1, Prx-2, CRP2/SmLIM and GATA family members, basic helix-loop-helix factors and their inhibitors of differentiation; and regulatory molecules include enzymes (matrix metalloproteinase (MMP), tissue plasminogen activator (PLAT or tPA), cyclooxygenase (COX), angiogenin), molecules regulating Notch signaling which consists of monoclonal antibodies to Notch ligands and receptors, RNA interference, antisense Notch, receptor and mastermind-like 1 (MAML1) decoys, beta and gamma-secretase inhibitors (GSI), or any other molecules that can activate or inhibit Notch signaling.

Vascular Endothelial Growth Factor (VEGF, also known as VEGF-A)

The term "VEGF" broadly encompasses two families of proteins that result from the alternate splicing of a single gene, VEGF, composed of 8 exons. The alternate splice sites reside in the exons 6, 7, and 8. However, the alternate splice site in the terminal exon 8 is functionally important. One family of proteins arise from the proximal splice site and are denoted ($VEGF_{xxx}$). Proteins produced by alternate splicing at this proximal location are PRO-angiogenic and are expressed conditionally (for instance, when tissues are hypoxic and secreted signals induce angiogenesis). The other family of proteins arise from the distal splice site and are denoted ($VEGF_{xxx}b$). Proteins produced by alternate splicing at this distal location are ANTI-angiogenic and are expressed in healthy tissues under normal conditions.

VEGF exons 6 and 7 contain splice sites (result in the inclusion or exclusion of exons 6 and 7) that affect heparin binding affinity and amino acid number. Humans comprise $VEGF_{121}$, $VEGF_{121}b$, $VEGF_{145}$, $VEGF_{165}$, $VEGF_{165}b$, $VEGF_{189}$, and $VEGF_{206}$. Heparin binding affinity, interactions with heparin surface proteoglycans (HSPGs) and neuropilin co-receptors on the cell surface mediated by amino acid sequences in exons 6 and 7 enhance the ability of VEGF variants to activate VEGF signaling receptors (VEGFRs).

Endogenous VEGF splice variants are released from cells as glycosylated disulfide-bonded dimers. Structurally VEGF belongs to the PDGF family of cysteine-knot growth factors comprising Placenta growth factor (PlGF), VEGF-B, VEGF-C and VEGF-D (the VEGF sub-family of growth factors). VEGF is sometimes referred to as VEGF-A to differentiate it from these related growth factors. The term "VEGF" used herein to describe the present invention is meant to refer to VEGF-A.

Members of the VEGF family stimulate cellular responses by binding to cell-surface tyrosine kinase receptors (the VEGFRs). VEGF-A binds to VEGFR-1 (also known as Flt-1) and VEGFR-2 (also known as KDR/Flk-1). VEGFR-2 is the predominant receptor for VEGF-A mediating almost all of the known cellular responses to this growth factor. The function of VEGFR-1 is unclear, although it is thought to modulate VEGFR-2 signaling. VEGFR-1 may also sequester VEGF from VEGFR-2 binding (which may be important during development).

Compositions, methods, and devices of the present invention comprise all VEGF polypeptides generated from alternative splicing including pro- and anti-angiogenic forms. Devices of the present invention administered to a subject contain only pro-angiogenic VEGF polypeptide splice forms. Alternatively, or in addition, devices of the present invention administered to a subject contain a mixture of pro- and anti-angiogenic VEGF polypeptide splice forms. Pro- and anti-angiogenic VEGF polypeptide splice forms are released by the scaffold composition of the device simultaneously or sequentially. For example, the opposing splice forms are released together in order to achieve a precise level of stimulation. Alternatively, the opposing splice forms are released sequentially to stimulate angiogenesis and subsequently attenuate the signal when the desired result has been achieved. In another embodiment, devices comprising pro-angiogenic VEGF polypeptide splice forms are placed at the target tissue site while devices comprising anti-angiogenic VEGF polypeptide splice forms are placed in surrounding tissues in order to prevent pro-angiogenic signals from disseminating into and stimulating non-target tissue.

Exemplary VEGF polypeptide splice forms comprised by the compositions, methods, and devices of the present invention include, but are not limited to, the polypeptides described by the following sequences and SED ID NOs. VEGF polypeptide splice forms are released from compositions, scaffolds, or devices of the present invention as naked, or glycosylated polypeptides. Alternatively, or in addition, VEGF polypeptide splice forms are monomers or disulfide-bonded dimers. In a preferred embodiment, VEGF polypeptide splice forms are released into target tissues from compositions, scaffolds, and/or devices of the present invention as glycosylated disulfide-bonded dimers.

Human $VEGF_{148}$ is encoded by the following amino acid sequence (NCBI Accession No. NP_001020540 and SEQ ID NO: 12):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe npcgpcserr khlfvqdpqt ckcsckntds rckm
```

Human $VEGF_{165}$ is encoded by the following amino acid sequence (NCBI Accession No. NP_001020539 and SEQ ID NO: 13):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
```

```
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe npcgpcserr khlfvqdpqt ckcsckntds rckarqleln
361 ertcrcdkpr r
```

Human VEGF$_{165}$b is encoded by the following amino acid sequence (NCBI Accession No. NP_001028928 and SEQ ID NO: 14):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe npcgpcserr khlfvqdpqt ckcsckntds rckarqleln
361 ertcrsltrk d
```

Human VEGF$_{183}$ is encoded by the following amino acid sequence (NCBI Accession No. NP_001020538 and SEQ ID NO: 15):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksrp cgpcserrkh lfvqdpqtck
361 cscknldsrc karqlelner tcrcdkprr
```

Human VEGF$_{189}$ is encoded by the following amino acid sequence (NCBI Accession No. NP_003367 and SEQ ID NO: 16):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksry kswsvpcgpc serrkhlfvq
361 dpqtckcsck ntdsrckarq lelnertcrc dkprr
```

Human VEGF$_{206}$ is encoded by the following amino acid sequence (NCBI Accession No. NP_001020537 and SEQ ID NO: 17):

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
```

```
-continued
121 geaavcadsa paarapqala rasgrggrva rrgaeesgpp hspsrrgsas ragpgraset 181 mnfllswvhw slalllylhh akwsqaapma egggqnhhev vkfmdvyqrs ychpietivd 241 ifqeypdeie yifkpscvpl mrcggccnde glecvptees nitmqimrik phqgqhigem 301 sflqhnkcec rpkkdrarqe kksvrgkgkg qkrkrkksry kswsvyvgar cclmpwslpg 361 phpcgpcser rkhlfvqdpq tckcsckntd srckarqlel nertcrcdkp rr
```

Gamma-Secretase Inhibitors (GSI)

Notch is a cell-surface receptor that regulates cell fate decisions throughout development and under selected conditions in adult tissues. Notch signaling results in widely variable outcomes depending on the cells and signaling molecules involved. However, it is generally known that binding of Notch ligands of the Delta and Jagged families results in the proteolytic cleavage of Notch. The Notch protein is first cleaved in the extracellular domain and then subsequently cleaved in the transmembrane domain. The second cleavage event is mediated by γ-secretase. Notch cleavage allows the intracellular domain of the receptor (the Notch IntraCellular Domain, NICD) to translocate to the nucleus where it regulates transcription. Thus, γ-secretase is a Notch activator.

Notch signaling is involved in angiogenesis and vascular remodeling. Moreover, Notch signaling regulates endothelial cell proliferation and migration events necessary to form new blood vessels during angiogenesis in normal tissues as well as malignant tumors. Methods of the present invention are drawn towards inducing angiogenesis in normal tissues, not malignant tissues. Furthermore, it is of great importance to avoid inducing a malignant state within a stable or benign tumor by introducing pro-angiogenic factors in the absence of factors to limit Notch activation. In one preferred embodiment of the present invention, pro-angiogenic factors are released from compositions, scaffolds, or devices, either simultaneously or sequentially, with notch-inhibitors, e.g. inhibitors of gamma-secretase (γ-secretase), to prevent stimulation of angiogenesis within neoplastic tissue.

Compositions, scaffolds, and devices of the present invention comprise all inhibitors of Notch activation to be released simultaneously or sequentially with pro-angiogenic factors. Inhibitors of Notch activity encompassed by the present invention block binding of one or more ligands to the Notch receptor. Alternatively, or in addition, inhibitors of Notch activity present intracellular signal transduction from the Notch receptor or cleavage of the Notch receptor polypeptide. Notch inhibitors of the present invention comprise endogenous or exogenous small molecules, compounds, single- or double-stranded RNA polynucleotides, single- or double-stranded DNA polynucleotides, polypeptides, antibodies, intrabodies, natural or synthetic ligands, genetically-engineered ligands, and genetically-manipulated γ-secretase proteins or fragments thereof. Exemplary inhibitors of Notch activation include, but are not limited to, monoclonal antibodies to Notch ligands and receptors, RNA interference, antisense Notch, receptor and mastermind-like 1 (MAML1) decoys, beta and gamma-secretase inhibitors (GSI).

Gamma-secretase is an integral membrane protein that is one part of a multi-subunit protease complex that cleaves single-pass transmembrane proteins at residues within the transmembrane domain. The gamma secretase complex comprises four individual proteins: presenilin, nicastrin, APH-1 (anterior pharynx-defective 1), and PEN-2 (presenilin enhancer 2). A fifth protein, known as CD147, is a non-essential regulator of the complex whose absence increases activity.

The proteins in the gamma secretase complex are heavily modified by proteolysis during assembly and maturation of the complex. Presenilin is an aspartyl protease comprising the catalytic subunit and is activated by autocatalytic cleavage of to N- and C-terminal fragments. Nicastrin maintains the stability of the assembled complex, regulates intracellular protein trafficking, and recognizes substrates via binding to the N-terminal ectodomain of the target protein. PEN-2 associates with the complex via binding of a transmembrane domain of presenilin and stabilizes the complex after presenilin proteolysis. APH-1, which is required for proteolytic activity, binds to the complex via a conserved alpha helix interaction motif and aids in initiating assembly of premature components.

The present invention comprises one or more inhibitors of γ-secretase which target one or more proteins of this complex and inhibit one or more functions of these proteins. Alternatively, or in addition, γ-secretase inhibitors of the present invention prevent assembly of the γ-secretase protease complex. Furthermore, contemplated γ-secretase inhibitors of the present invention inhibit intracellular signal transduction from an assembled γ-secretase protease complex. Contemplated γ-secretase inhibitors of the present invention bind one or more proteins of the g-secretase complex and partially or entirely block an activity or function. Exemplary γ-secretase inhibitors of the present invention decrease, prevent, or delay activation, as well as inactivate one or more protease components. Exemplary γ-secretase inhibitors of the present invention desensitize or down regulate the activity or expression of one or more proteins of the γ-secretase complex. Exemplary γ-secretase inhibitors of the present invention consist of, consist essentially of, or comprise endogenous or exogenous small molecules, compounds, single- or double-stranded RNA polynucleotides, single- or double-stranded DNA polynucleotides, polypeptides, antibodies, intrabodies, natural or synthetic ligands, genetically-engineered ligands, and genetically-manipulated γ-secretase proteins or fragments thereof.

Exemplary γ-secretase inhibitors of the present invention include, but are not limited to, DAFT and N-[N-(3,5-Difluorophenacetyl-L-alanyl)]-S-phenylglycine t-butyl ester.

Cell-Mediated Enzymatic Scaffold Degradation

Cells secrete enzymes that degrade the material of the scaffold, thereby controlling the rate at which cells exit the scaffold. Cells within close proximity to the implanted scaffold composition secrete enzymes, such as collagenases and plasmin, which degrade the polymer composition. This property is used in certain embodiments to control the release of bioactive compositions into the local cellular environment. The rate of release of bioactive composition may thus be regulated by controlling the density and susceptibility to these enzymes of oligopeptides used as either cross-links in the material or as components of the main chains. Certain materials are degraded in a preprogrammed manner independent of cell action (e.g. hydrolytic degradation of poly(lactide-co glyolide) as a degradable scaffold. The scaffolds may be prepared such that the degradation time may be controlled by using a mixture of degradable components in proportions to achieve a desired degradation rate. Scaffold compositions are sensitive to degradation by materials secreted by the cells located immediately adjacent to the scaffold. One example of this is the use of metalloproteinase (MMP)-sensitive substrate in the scaffold matrix; bioactive composition is released when the adjacent cells have secreted sufficient MMP to begin degradation of the matrix.

Scaffold Compositions and Architecture

Components of the scaffolds are organized in a variety of geometric shapes (e.g., beads, pellets), niches, planar layers (e.g., thin sheets). For example, multicomponent scaffolds are constructed in concentric layers each of which is characterized by different physical qualities (% polymer, % crosslinking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, proliferation, differentiation, elaboration of secreted factors or enzymes, or migration.

Cells incubated in the scaffold are educated and induced to migrate out of the scaffold to directly affect a target tissue, e.g., and injured tissue site. For example, stromal vascular cells and smooth muscle cells are useful in sheet-like structures are used for repair of vessel-like structures such as blood vessels or layers of the body cavity. For example, such structures are used to repair abdominal wall injuries or defects such as gastroschisis. Similarly, sheet-like scaffolds seeded with dermal stem cells and/or keratinocytes are used in bandages or wound dressings for regeneration of dermal tissue. The device is placed or transplanted on or next to a target tissue, in a protected location in the body, next to blood vessels, or outside the body as in the case of an external wound dressing. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by sequentially injecting or inserting matrix materials. Scaffold devices are optionally recharged with cells or with bioactive compounds, e.g., by sequential injection or spraying of substances such as growth factors or differentiation factors.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold vary according to the application or tissue type for which regeneration is sought. It is biodegradable (e.g., collagen, alginates, polysaccharides, polyethylene glycol (PEG), poly(glycolide) (PGA), poly(L-lactide) (PLA), or poly(lactide-co-glycolide) (PLGA) or permanent (e.g., silk) In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogenous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agent, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds are controlled by scaffold formulation to present morphogens in a spatially and temporally controlled manner. This controlled release not only eliminates systemic side effects and the need for multiple injections, but can be used to create a microenvironment that activates host cells at the implant site.

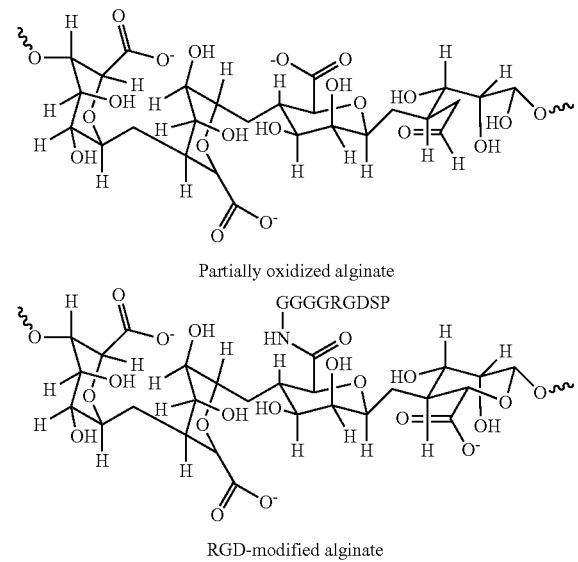

The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

The scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference discloses methods for making and using polymers containing polysachharides such as alginates or modified alginates that are particularly useful for cell transplantation and tissue engineering applications.

Useful polysaccharides other than alginates include agarose and microbial polysaccharides such as those listed in the table below.

| Polysaccharide Scaffold Compositions | |
|---|---|
| Polymers[a] | Structure |
| Fungal | |
| Pullulan (N) | 1,4-;1,6-α-D-Glucan |
| Scleroglucan (N) | 1,3;1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-;1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2;1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N-neutral, A = anionic and C = cationic.

The scaffolds of the invention are porous or non-porous. For example, the scaffolds are nanoporous having a diameter of less than about 10 nm; microporous wherein the diameter of the pores are preferably in the range of about 100 nm-20 μm; or macroporous wherein the diameter of the pores are greater than about 20 μm, more preferably greater than about 100 μm and even more preferably greater than about 400 μm. In one example, the scaffold is macroporous with aligned pores of about 400-500 μm in diameter. Other methods of preparing porous hydrogel products are known in the art. (U.S. Pat. No. 6,511,650 incorporated herein by reference).

Bioactive Compositions

The device includes one or more bioactive compositions. Bioactive compositions are purified naturally-occurring, synthetically produced, or recombinant compounds, e.g., polypeptides, nucleic acids, small molecules, or other agents. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

The bioactive composition comprises an element to improve a function of the scaffold composition or to promote angiogenesis. For example, at least one cell adhesion molecule is incorporated into or onto the polymer matrix to attach the scaffold composition to the local tissue site and prevent diffusion of the device. Such molecules are incorporated into the polymer matrix prior to polymerization of the matrix or after polymerization of the matrix. Examples of cell adhesion molecules include, but are not limited to, peptides, proteins and polysaccharides. More specifically, cell adhesion molecules include, but are not limited to, fibronectin, laminin, collagen, thrombospondin 1, vitronectin, elastin, tenascin, aggrecan, agrin, bone sialoprotein, cartilage matrix protein, fibrinogen, fibrin, fibulin, mucins, entactin, osteopontin, plasminogen, restrictin, serglycin, SPARC/osteonectin, versican, von Willebrand Factor, polysaccharide heparin sulfate, connexins, collagen, RGD (Arg-Gly-Asp) and YIGSR (Tyr-Ile-Gly-Ser-Arg) (SEQ ID NO: 9) peptides and cyclic peptides, glycosaminoglycans (GAGs), hyaluronic acid (HA), condroitin-6-sulfate, integrin ligands, selectins, cadherins and members of the immunoglobulin superfamily. Other examples include neural cell adhesion molecules (NCAMs), intercellular adhesion molecules (ICAMs), vascular cell adhesion molecule (VCAM-1), platelet-endothelial cell adhesion molecule (PECAM-1), L1, and CHL1.

Examples of some of these molecules and their function are shown in the following table.

| ECM Proteins and peptides and role in cell function | | | |
|---|---|---|---|
| Protein | Sequence | Seq. ID No: | Role |
| Fibronectin | RGDS | | Adhesion |
| | LDV | | Adhesion |
| | REDV | | Adhesion |
| Vitronectin | RGDV | | Adhesion |
| Laminin A | LRGDN | 7 | Adhesion |
| | IKVAV | 8 | Neurite extension |
| Laminin B1 | YIGSR | 9 | Adhesion of many cells, via 67 kD laminin receptor |
| | PDSGR | 10 | Adhesion |
| Laminin B2 | RNIAEIIKDA | 11 | Neurite extension |
| Collagen 1 | RGDT | | Adhesion of most cells |
| | DGEA | | Adhesion of platelets, other cells |
| Thrombospondin | RGD | | Adhesion of most cells |
| | VTXG | | Adhesion of platelets |

Hubbell, J A (1995): Biomaterials in tissue engineering. Bio/Technology 13: 565-576. One-letter abbreviations of amino acids are used, X stands for any amino acid.

Additional examples of suitable cell adhesion molecules are shown below.

Amino acid sequences specific for proteoglycan binding from extracellular matrix proteins

| SEQUENCE | SEQ. ID. NO. | PROTEIN |
|---|---|---|
| XBBXBX* | 2 | Consensus sequence |
| PRRARV | 3 | Fibronectin |
| YEKPGSPPREVVPRPRPGV | 4 | Fibronectin |
| RPSLAKKQRFRHRNRKGYRSQRGHSRGR | 5 | Vitronectin |
| RIQNLLKITNLRIKFVK | 6 | Laminin |

Particularly preferred cell adhesion molecules are peptides or cyclic peptides containing the amino acid sequence arginine-glycine-aspartic acid (RGD) which is known as a cell attachment ligand and found in various natural extracellular matrix molecules. A polymer matrix with such a modification provides cell adhesion properties to the scaffold, and sustains long-term survival of mammalian cell systems, as well as supporting cell growth.

Coupling of the cell adhesion molecules to the polymer matrix is accomplished using synthetic methods which are in general known to one of ordinary skill in the art and are described in the examples. Approaches to coupling of peptides to polymers are discussed in Hirano and Mooney, Advanced Materials, p. 17-25 (2004). Other useful bonding chemistries include those discussed in Hermanson, Bioconjugate Techniques, p. 152-185 (1996), particularly by use of carbodiimide couplers, DCC and DIC (Woodward's Reagent K). Since many of the cell adhesion molecules are peptides, they contain a terminal amine group for such bonding. The amide bond formation is preferably catalyzed by 1-ethyl-3-(3-dimethylaminopropyl)carbodiimide (EDC), which is a water soluble enzyme commonly used in peptide synthesis. The density of cell adhesion ligands, a critical regulator of cellular phenotype following adhesion to a biomaterial. (Massia and Hubbell, J. Cell Biol. 114:1089-1100, 1991; Mooney et al., J. Cell Phys. 151:497-505, 1992; and Hansen et al., Mol. Biol. Cell 5:967-975, 1994) can be readily varied over a 5-order of magnitude density range.

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophillization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device is assembled in vivo in several ways. The scaffold is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and cells prior to introduction into the body or while it is introduced. The resultant in vivo/in situ assembled scaffold contains a mixture of these substances and cells.

In situ assembly of the scaffold occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an amphiphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A. 99:5133-5138. A method for reversible gellation following shear thinning is exemplified in Lee et al., 2003, Adv. Mat. 15:1828-1832.

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances. Alternatively, compartments self-organize based on their hydro-philic/phobic characteristics or on secondary interactions within each compartment.

Compartmentalized Device

A compartmentalized device is designed and fabricated using different compositions or concentrations of compositions for each compartment. For example, a first bioactive composition is encapsulated within hydrogels, using standard encapsulation techniques (e.g., alginate microbead formation). This compartment is then coated with a second layer of gel (e.g., double layered alginate microbeads). This second compartment is formed from the same material that contains bioactive composition elements, the same material in a distinct form (e.g., varying mechanical properties or porosity), or a completely different material that provides appropriate chemical/physical properties.

Alternatively, the compartments are fabricated individually, and then adhered to each other (e.g., a "sandwich" with an inner compartment surrounded on one or all sides with the second compartment). This latter construction approach is accomplished using the intrinsic adhesiveness of each layer for the other, diffusion and interpenetration of polymer chains in each layer, polymerization or cross-linking of the second layer to the first, use of an adhesive (e.g., fibrin glue), or physical entrapment of one compartment in the other. The compartments self-assemble and interface appropriately, either in vitro or in vivo, depending on the presence of appropriate precursors (e.g., temperature sensitive oligopeptides, ionic strength sensitive oligopeptides, block polymers, cross-linkers and polymer chains (or combinations thereof), and precursors containing cell adhesion molecules that allow cell-controlled assembly). An individual with ordinary skill in the art of stem cell biology and biomaterials can readily derive a number of potentially useful designs for combining or separating components of a bioactive composition.

Alternatively, the compartmentalized device is formed using a printing technology. Successive layers of a scaffold precursor doped with bioactive substances and/or cells is placed on a substrate then cross linked, for example by self-assembling chemistries. When the cross linking is controlled by chemical-, photo- or heat-catalyzed polymerization, the thickness and pattern of each layer is controlled by a masque, allowing complex three dimensional patterns to be built up when un-cross-linked precursor material is washed away after each catalyzation. (WT Brinkman et al., Photo-cross-linking of type 1 collagen gels in the presence of smooth muscle cells: mechanical properties, cell viability, and function. Biomacromolecules, 2003 July-August; 4(4): 890-895; W. Ryu et al., The construction of three-dimensional microfluidic scaffolds of biodegradable polymers by solvent vapor based bonding of micro-molded layers. Biomaterials, 2007 February; 28(6): 1174-1184; Wright, Paul K. (2001). 21st Century manufacturing. New Jersey: Prentice-Hall Inc.) Complex, multi-compartment layers are also built up using an inkjet device which "paints" different doped-scaffold precursors on different areas of the substrate. Julie Phillippi (Carnegie Mellon University) presentation at the annual meeting of the American Society for Cell Biology on Dec. 10, 2006; Print me a heart and a set of arteries, Aldhouse P., New Scientist 13 Apr. 2006 Issue 2547 p 19; Replacement organs, hot off the press, C. Choi, New Scientist, 25 Jan. 2003, v2379. These layers are built-up into complex, three dimensional compartments. The device is also built using any of the following methods: Jetted Photopolymer, Selective Laser Sintering, Laminated Object Manufacturing, Fused Deposition Modeling, Single Jet Inkjet, Three Dimensional Printing, or Laminated Object Manufacturing.

Growth Factors and Incorporation of Compositions into/onto a Scaffold Device

Bioactive substances that influence growth, development, movement, and other cellular functions are introduced into or onto the scaffold structures. Such substances include BMP, bone morphogenetic protein; ECM, extracellular matrix proteins or fragments thereof; EGF, epidermal growth factor; FGF-2, fibroblast growth factor 2; NGF, nerve growth factor; PDGF, platelet-derived growth factor; PlGF, placental growth factor; TGF, transforming growth factor, and VEGF, vascular endothelial growth factor. Cell-cell adhesion molecules (cadherins, integrins, ALCAM, NCAM, proteases) are optionally added to the scaffold composition.

Exemplary growth factors and ligands are provided in the tables below.

| Growth factors used for angiogenesis | | |
|---|---|---|
| Growth factor | Abbreviation | Relevant activities |
| Vascular endothelial growth factor | VEGF | Migration, proliferation and survival of ECs |
| Basic fibroblast growth factor | bFGF-2 | Migration, proliferation and survival of ECs and many other cell types |
| Platelet-derived growth factor | PDGF | Promotes the maturation of blood vessels by the recruitment of smooth muscle cells |
| Angiopoietin-1 | Ang-1 | Strengthens EC-smooth muscle cell interaction |
| Angiopoietin-2 | Ang-2 | Weakens EC-smooth muscle cell interaction |
| Placental growth factor | PlGF | Stimulates angiogenesis |
| Transforming growth factor | TGF | Stabilizes new blood vessels by promoting matrix deposition |

| Growth factors used for wound healing | | |
|---|---|---|
| Growth Factor | Abbreviation | Relevant activities |
| Platelet-derived growth factor | PDGF | Active in all stages of healing process |
| Epidermal growth factor | EGF | Mitogenic for keratinocytes |
| Transforming growth factor-β | TGF-β | Promotes keratinocyte migration, ECM synthesis and remodeling, and differentiation of epithelial cells |
| Fibroblast growth factor | FGF | General stimulant for wound healing |

| Growth Factors Used for Tissue-Engineering | | | | |
|---|---|---|---|---|
| Growth factor | Abbreviation | Molecular weight (kDa) | Relevant activities | Representative supplier of rH growth factor |
| Epidermal growth factor | EGF | 6.2 | Proliferation of epithelial, mesenchymal, and fibroblast cells | PeproTech Inc. (Rocky Hill, NJ, USA) |
| Platelet-derived growth factor | PDGF-AA | 28.5 | Proliferation and chemoattractant agent for smooth muscle cells; extracellular matrix synthesis and deposition | PeproTech Inc. |
| | PDGF-AB | 25.5 | | |
| | PDGF-BB | 24.3 | | |
| Transforming growth factor-α | TFG-α | 5.5 | Migration and proliferation of keratinocytes; extracellular matrix synthesis and deposition | PeproTech Inc. |
| Transforming growth factor-β | TGF-β | 25.0 | Proliferation and differentiation of bone forming cells; chemoattractant for fibroblasts | PeproTech Inc. |

Growth Factors Used for Tissue-Engineering

| Growth factor | Abbreviation | Molecular weight (kDa) | Relevant activities | Representative supplier of rH growth factor |
|---|---|---|---|---|
| Bone morphogenetic protein | BMP-2<br>BMP-7 | 26.0<br>31.5 | Differentiation and migration of bone forming cells | Cell Sciences Inc. (Norwood, MA, USA) |
| Basic fibroblast growth factor | bFGF/FGF-2 | 17.2 | Proliferation of fibroblasts and initiation of angiogenesis | PeproTech Inc. |
| Vascular endothelial growth factor | $VEGF_{165}$ | 38.2 | Migration, proliferation, and survival of endothelial cells | PeproTech Inc. | rH, recombinant human

Immobilized ligands used in tissue engineering

| Immobilized ligand* | ECM molecule source | Application |
|---|---|---|
| RGD | Multiple ECM molecules, including fibronectin, vitronectin, laminin, collagen and thrombospondin | Enhance bone and cartilage tissue formation in vitro and in vivo<br>Regulate neurite outgrowth in vitro and in vivo<br>Promote myoblast adhesion, proliferation and differentiation<br>Enhance endothelial cell adhesion and proliferation |
| IKVAV (SEQ ID NO: 8), YIGSR (SEQ ID NO: 9), RNIAEIIKDI (SEQ ID NO: 11) | Laminin | Regulate neurite outgrowth in vitro and in vivo |
| Recombinant fibronectin fragment ($FNIII_{7-10}$) | Fibronectin | Promote formulation of focal contacts in pre-osteoblasts |
| Ac-GCRDGPQ-GIWGQDRCG (SEQ ID NO: 18) | Common MMP substrates, (e.g. collagen, fibronectin, laminin) | Encourage cell-mediated proteolytic degradation, remodeling and bone regeneration (with RGD and BMP-2 presentation) in vivo |

*Sequences are given in single-letter amino acid code. MMP, matrix metalloproteinase.

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective cell delivery by the device is desired.

Carrier systems for tissue regeneration are described in the table below.

Polymeric carriers used to deliver various growth factors and the type of tissues regenerated

| Growth factor | Carrier | Tissue regenerated |
|---|---|---|
| EGF | Gelatin | Dermis |
|  | PET suture | Tendon |
|  | PVA sponge | Dermis |
| PDGF | Chitosan-PLLA scaffold | Craniofacial bone |
|  | CMC gel | Dermis |
|  | Fibrin | Ligament |
|  | Porous HA | Long Bone |
| TGF-β | Alginate | Cartilage |
|  | PLA | Long Bone |
|  | CaP-titanium mesh | Craniofacial bone |
|  | Polyoxamer; PEO gel | Dermis |
| rhBMP-2 | Collagen sponge | Long bone |
|  |  | Craniofacial bone |
|  | HA-TCP granules | Spinal bone |
|  | HA-collagen | Long bone |
|  | PLA-DX-PEG | Ectopic and hip bone |
| rHBMP-7 | HA | Spinal bone |
|  | Collagen-CMC | Spinal bone |
|  | Porous HA | Craniofacial bone |
| bFGF | Chitosan | Dermis |
|  | Heparin-alginate | Blood vessels |
|  | EVAc microspheres | Blood vessels |
|  | Fibrin matrices | Blood vessels |
| VEGF | PLG scaffold | Blood vessels |
|  | PLG scaffold | Blood vessels |
|  | PLG microspheres | Blood vessels |
|  | Fibrin mesh | Blood vessels |

Abbreviations:
PET, poly (ethylene terepthalate);
PVA, polyvinyl alcohol;
PLLA, poly(L-lactic acid);
CMC, carboxymethylcellulose;
HA, hydroxyapatite;
PLA, poly(D,L-lactic acid);
CaP, calcium phosphate;
PEO, poly (ethylene oxide);
TCP, tricalcium phosphate;
PEG, poly(ethylene glycol);
-DX-, -p-dioxanone-;
EVAc, ethylene vinyl acetate;
PLG, poly (lactide-co-glycolide).

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, long-term presentation of a bioactive substance on the scaffold in a defined conformation. Exemplary reagents for covalent coupling of such substances are provided in the table below.

| Methods to covalently couple peptides/proteins to polymers | | |
|---|---|---|
| Functional Group of Polymer | Coupling reagents and cross-linker | Reacting groups on proteins/peptides |
| —OH | Cyanogen bromide (CNBr) Cyanuric chloride 4-(4,6-Dimethoxy-1,3,5-triazin-2-yl)-4-methyl-morpholinium chloride (DMT-MM) | —$NH_2$ |
| —$NH_2$ | Diisocyanate compounds Diisothoncyanate compounds Glutaraldehyde Succinic anhydride | —$NH_2$ —OH |
| —$NH_2$ | Nitrous Acid Hydrazine + nitrous acid | —$NH_2$ —SH —Ph—OH |
| —$NH_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —$NH_2$ |
| —SH | Disulfide compound | —SH |

[a]EDC: 1-ethyl-3-(3-dimethylaminopropyl) carbodiimide hydrochloride;
DCC: dicyclohexylcarbodiimide The following materials and methods were used to generate the data described herein.

Preparation and Loading of Polymer/Gel Compositions

Ultrapure alginates were purchased from ProNova Biomedical (Norway). MVG alginate, a high-G-containing alginate (M/G ratio of 40/60 as specified by the manufacturer), was used as the high molecular weight (molecular mass=250,000 Da) component to prepare gels. Low molecular weight alginate (molecular mass=50,000 Da) was obtained by gamma-irradiating high molecular weight alginate with a cobalt-60 source for 4 h at a gamma-dose of 3.0 Mrad (Radiation Lab, Massachusetts Institute of Technology). The alginate used to form gels was a combination of the two different molecular weight polymers at a ratio of 3:1. Both alginate polymers were diluted to 1% w/v in double-distilled $H_2O$, and 1% of the sugar residues in the polymer chains were oxidized with sodium periodate (Aldrich, St Louis, Mo.) by maintaining solutions in the dark for 17 h at room temperature. An equimolar amount of ethylene glycol (Fisher, Pittsburgh, Pa.) was added to stop the reaction, and the solution was subsequently dialyzed (MWCO 1000, Spectra/Por, Rancho Dominguez, Calif.) over 3 days. The solution was sterile filtered, frozen (−20 degree C. overnight), lyophilized and stored at −20 degree C. To prepare gels, modified alginates were reconstituted in EBM-2 (Lonza, Walkersville, Md.) to obtain a 2% w/v solution(75% low molecular weight, 25% high molecular weight MVG used in all experiments) prior to gelation. The 2% w/v alginate solutions were cross-linked with aqueous slurries of a calcium sulfate solution (0.21 g $CaSO_4$ mL/L distilled H20) at a ratio of 25:1 (40 microliter of CaSO4 per 1 mL of 2% w/v alginate solution) using a 1 mL syringe. Reconstituted alginate was stored at 4 degree C. For incorporation of VEGF, PDGF and DAPT, alginate solutions were mixed with recombinant human VEGF 165, PDGF-BB (R&D systems, MN) or DAPT (N—[N-(3,5-Difluorophenacetyl-L-alanyl)]-Sphenylglycine t-Butyl Ester) (EMD Chemicals, NJ) by using two syringes coupled by a syringe connector. Calcium slurry (Sigma, St Louis, Mo.) was then mixed with the resulting alginate solution using two syringes coupled by a syringe connector to facilitate the mixing process and prevent entrapment of air bubbles during mixing. The mixture was allowed to gel for 30 min, and then was maintained at 4 degrees C. prior to animal injections.

Murine Hindlimb Model of Ischemia

The animals used were 6-week old severe combined immunodeficiency (SCID) mice on a C57BL/6J background (Jackson Laboratory, ME). Unilateral hindlimb ischemia was created as follows. The animals were anesthetized by intraperitoneal injections of ketamine (80 mg/kg) and xylazine (5 mg/kg). The external iliac and femoral artery and vein were ligated, and 50 μL alginate hydrogel incorporating 3 μg VEGF and/or 86-8600 ng DAPT was injected near the distal end of the ligation site. As controls, VEGF and DAPT in PBS were also injected intramuscularly or intraperitoneally (bolus delivery). Incisions were closed by 5-0 Ethicon sutures (Johnson & Johnson, N.J.). Blood flow in the hindlimb was monitored by a laser Doppler perfusion imaging (LDP/) system (Perimed AB, Sweden), and the results were normalized to the control unligated limb of the same animal.

Histology and Immunohistochemistry

Hindlimb muscle tissues between the two suture knots defining the ligation site were dissected and fixed by Z-fix (Anatech, M/) overnight and changed into 70% EtOH for storage prior to histology processing. Samples were embedded in paraffin and sectioned (5 μm thick) onto slides by Paragon (Paragon Bioservices, MD). Sections were incubated with primary anti-mouse CD31 antibody (1:250) (Pharmingen, Calif.) or α-smooth muscle actin antibody, followed by incubation with an anti-rat mouse biotinylated secondary (1:200) (Vector Laboratories, CA), and amplified by a Tyramide Signal Amplification (TSA) Biotin System (Perkin Elmer Life Sciences, MA). Staining was developed using DAB+ substrate chromogen (DAKO, CA) and counterstained with Mayer's Hematoxylin. Capillary densities were quantified by counting the CD31 positive capillary numbers, normalized to the tissue area, in 30 randomly chosen high-power (200×, 400×) fields. Images were captured with an Olympus-IX81 light microscope connected to an Olympus DP70 digital image capture system.

EXAMPLE 1

In vitro Model to Test the Significance of a Controlled Local Concentration of VEGF Endothelial cells isolated from diabetics are shown to have a reduced response to VEGF as compared to age-matched non-diabetics (FIG. 1, *$P<0.05$), as reflected in their capability of forming sprouts, the first step in angiogenesis. In addition, there is an optimal VEGF concentration to induce most sprouts. This suggests the need of a controlled concentration of growth factors in the local area to reach the best therapeutic effect.

EXAMPLE 2

In vitro Model to Test the Significance of a Combination of DAPT and VEGF

Figure 2:
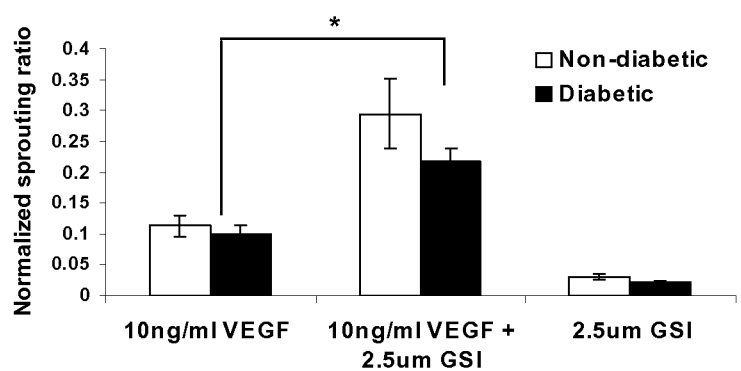
FIG. 2 is a bar graph showing the effect of VEGF and GSI on sprouting ratio. In vitro model was used to test the significance of a combination of DAPT and VEGF.

Endothelial cells isolated from diabetics produce more sprouts in the presence of a combination of both gamma-secretase inhibitors with VEGF. (FIG. 2, *$P<0.05$) than with either of them alone, which implies the need of a combination of both growth factor and DAPT.

EXAMPLE 3

Figure 3:
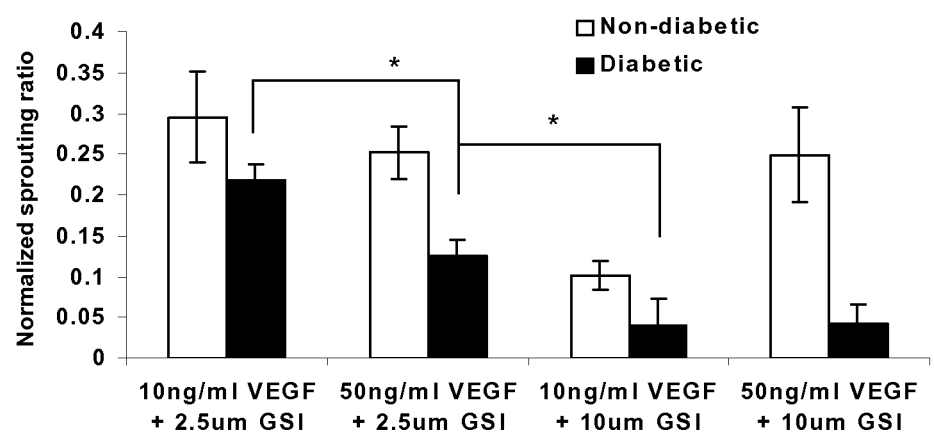
FIG. 3 is a bar graph showing the effect of different amounts and ratios of amounts of VEGF and GSI on sprouting ratio. In vitro model establishing the significance of a distinct presentation of VEGF and DAPT.

In vitro Model Establishing the Significance of a Distinct Presentation of VEGF and DAPT This examples illustrates the concept that while the combination of VEGF and DAPT is superior to either single factor alone, the optimal concentration for each individual compound does not coincide. As shown in FIG. 3 (*$P<0.05$), the concentration of VEGF that gives the most sprouts if used alone (50 ng/ml) is less superior to a lower concentration (10 ng/ml) when in combined use with DAPT (2.5 µM). Moreover, increasing both the concentration of VEGF (50 ng/ml) and DAPT (10 µM) actually reduces the number of sprouts. This indicates that the presentation of VEGF and DAPT may need to be separately controlled to achieve an optimal effect.

EXAMPLE 4

Figure 4:
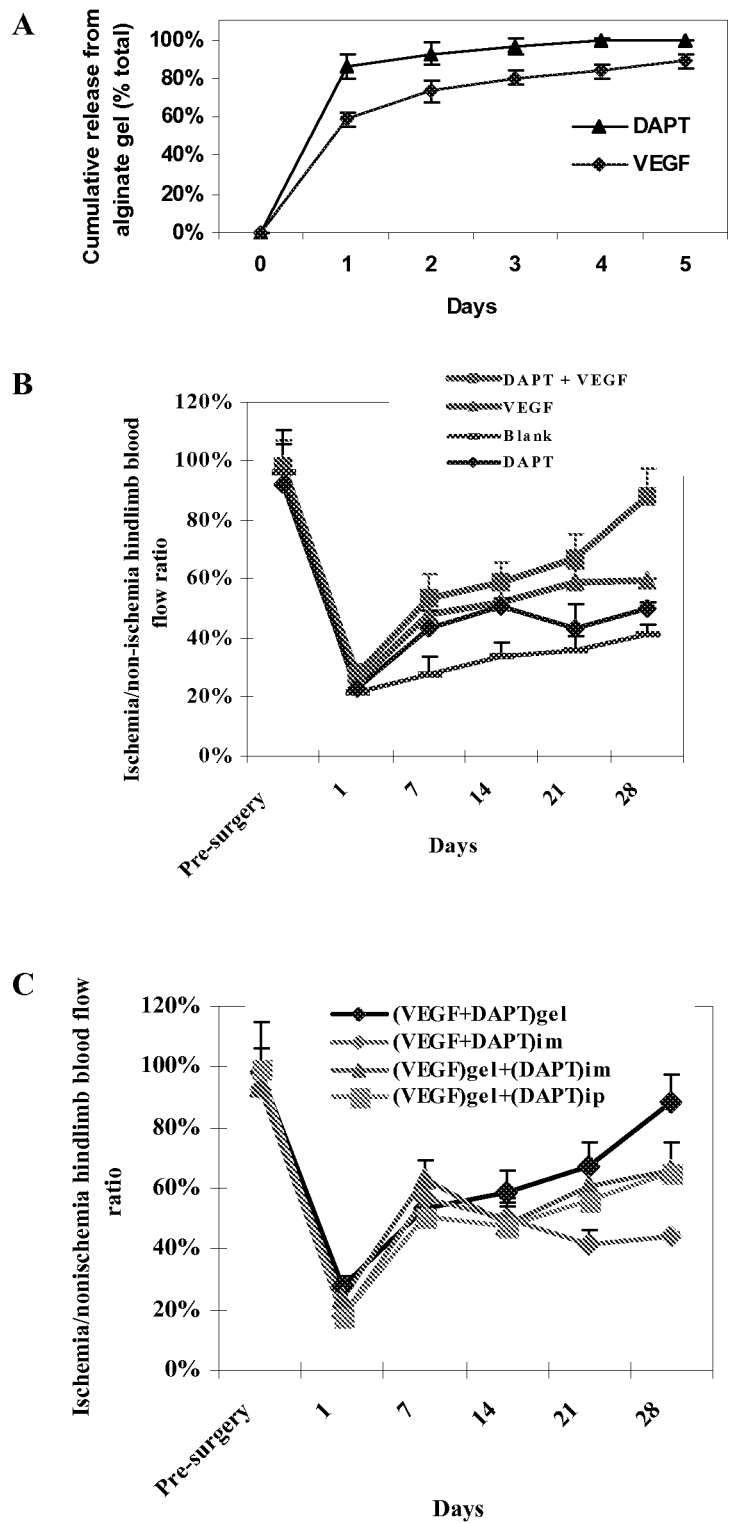
FIGS. 4A-C are a series of line graphs showing the effect of VEGF and a GSI (DAPT) on angiogenesis. 4A, In vitro release profiles of VEGF and DAPT from injected alginate hydrogel system; 4B and 4C, In vivo model to test the effect of controlled presentation of VEGF and DAPT to recover blood flow in an ischemia situation. Blood flow recovery subject to hindlimb ligation. gel: represents the use of the alginate as the delivery vehicle. im: intramuscular injection. ip: intraperitoneal injection.
Figure 6:
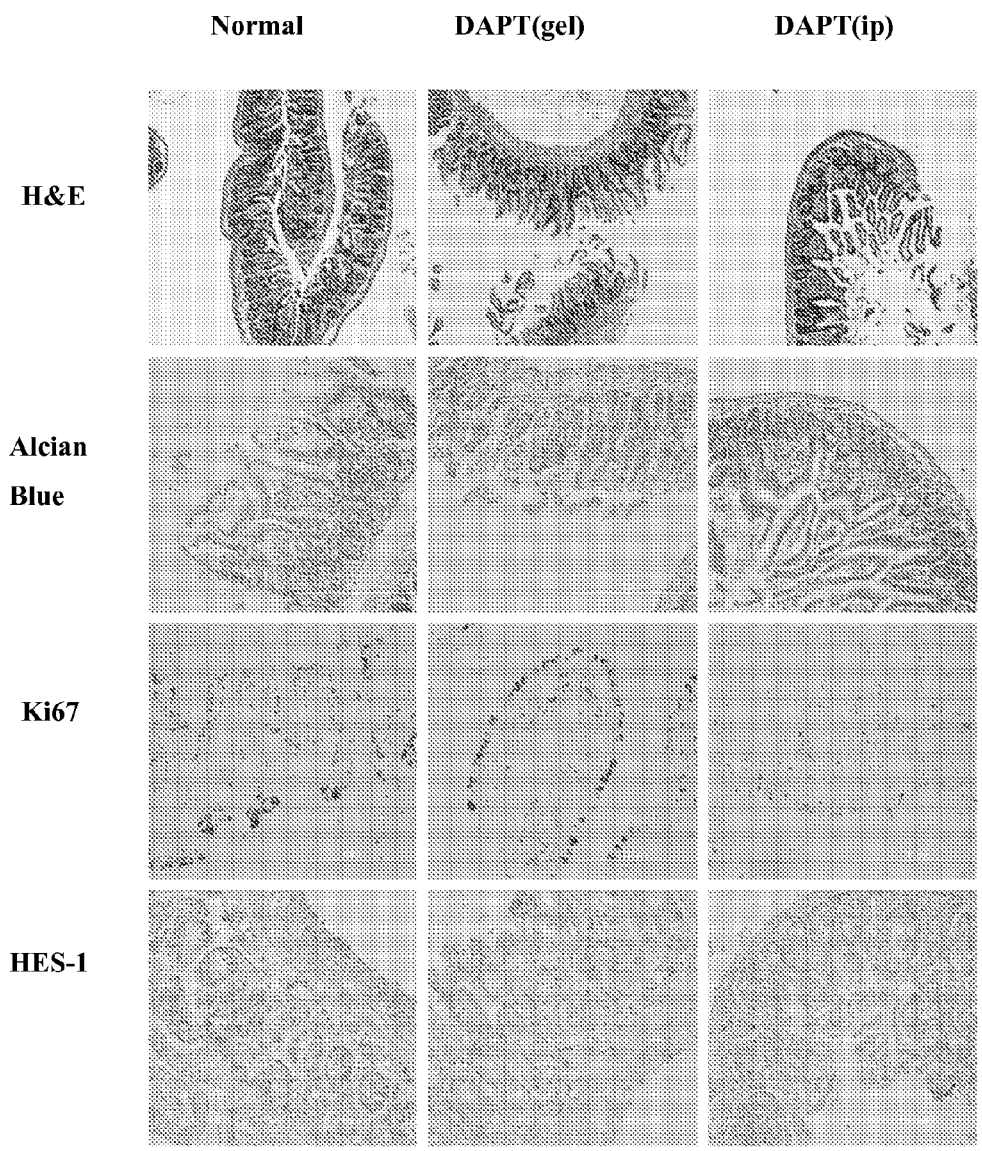
FIG. 6 is a series of photomicrographs showing the effect of DAPT on gastrointestinal tissue. In vivo model was used to test the effect of DAPT delivered from alginate gel system and from intraperitoneal injection on the cells in small intestines. gel: alginate gel. ip: intraperitoneal injection. H&E, alcian blue, Ki67 and HES-1 are the four different staining methods to characterize the crypt cells in small intestines. Ki-67 was used to stain the proliferative cells. Loss of Notch signaling can alter the proliferation rate of crypt cells. HES-1 staining was to examine the expression of a known Notch target gene in crypts. Alcian blue staining was to examine the deposition of glycosaminoglycan molecules. Loss of Notch signaling can result in more deposition of glycosaminoglycan molecules. Expression of HES-1 (hairy and enhancer of split 1), a member of basic helix-loop-helix family of transcription factors and a known Notch target gene in crypts was examined. Loss of Notch signaling can alter the proliferation rate of crypt cells, as shown by Ki-67 staining the proliferative cells. In addition, Notch inhibition has been reported to alter the balance between proliferative crypt cells and goblet cells, resulting in more deposition of glycosaminoglycan molecules, as characterized by alcian blue staining Notch inhibition can also result in a significant alteration of the morphology of the small intestine as compared to controls, as demonstrated by hematoxylin and eosin (H&E) staining.

In vivo Model to Test the Effect of Controlled Presentation of VEGF and DAPT to Recover Blood Flow in an Ischemia Situation Alginate is used as the delivery vehicle. Injectable alginate hydrogels incorporating VEGF and GSI is injected into the hindlimb ischemia site created by femoral artery and vein ligation in a murine model. Release profiles of VEGF and DAPT from alginate hydrogels are distinct, as shown in FIG. 4A. Blood flow before and after ligation surgery is measured by laser doppler perfusion imaging (LDPI) to indicate the extent of angiogenesis in the ischemia area. As shown in FIGS. 4B and 4C, (*$P<0.05$), when DAPT and VEGF are both incorporated in the alginate hydrogel the blood flow recovery is superior to simple bolus injection of them together, either drug alone from alginate gel or by bolus injection (including direct intramuscular and intraperitoneal injection), and blank control. This points to the significance of a controlled presentation of multiple pro-angiogenic compounds as compared to bolus injection.

EXAMPLE 5

In vivo Model to Test the Effect of Controlled Presentation of VEGF and DAPT on Newly-Formed Blood Vessel Density in an Ischemia Situation A combination of VEGF and DAPT delivered by alginate gel systems gave rise to the highest blood vessel density as compared to blank control, either alone released from gels (FIG. 5A), or administered via intramuscular or intraperitoneal injection (FIG. 5B). These data indicate the significance of controlled delivery of both VEGF and DAPT by the alginate gel system, i.e. controlled and coordinated release of growth factors and signaling molecules leads to an improved clinical result compared to conventional delivery methods.

EXAMPLE 6

In vivo Evaluation of the Effect of DAPT Delivered From Alginate Gel System and From Intraperitoneal Injection on the Cells in Small Intestines As compared to normal controls, DAPT delivered from alginate gel system does not alter cell differentiation at distant sites as much as DAPT delivered via intraperitoneal injection (DAPT delivered via injection disrupts normal intestinal structure, as indicated by H&E staining, presence of extra glycosaminoglycans by alcian blue staining, loss of proliferating cells by Ki67 staining, and downregulation of Notch target gene expression by HES-1 staining) DAPT delivered from the gel system only has effects in the local region while DAPT delivered via intraperitoneal injection goes into the systemic circulation and led to adverse effects at distant organs (e.g., small intestines as an example). These data indicate that a controlled local but not systemic presentation of delivered DAPT is a preferred delivery method.

EXAMPLE 7

Blood Vessel Density and Blood Flow Recovery

In vivo evaluation of the effect of controlled presentation of VEGF and DAPT on newly formed blood vessel density and blood flow recovery was carried out in an ischemic type I diabetic mouse model. The results (FIGS. 7A-B) indicate that a combination of controlled delivery of a prescribed previously determined ratio, e.g., an optimal level, of VEGF and DAPT increased the blood vessel density and recovered blood flow.

EXAMPLE 8

Comparison of Controlled Presentation of Factors Compared to Delivery of Factors Alone The effect of controlled presentation of VEGF and PDGF on newly formed blood vessel density and blood flow recovery was evaluated in vivo using the ischemic type I diabetic mouse model. The results (FIGS. 8A-B) indicate that a combination of optimal level of VEGF and PDGF is superior to VEGF or PDGF alone in recovering blood flow.

EXAMPLE 9

Controlled Presentation of a Combination of Factors VEGF, PDGF and DAPT on Angiogenesis In vivo evaluation of the effect of controlled presentation of VEGF, PDGF and DAPT on newly formed blood vessel density and blood flow recovery was carried out in an ischemic type I diabetic mouse model. These results (FIGS. 9A-B) indicate that a combination of optimal level of VEGF and DAPT is superior to a combination of VEGF and PDGF in recovering blood flow.

EXAMPLE 10

Maturation of Newly Formed Blood Vessels

Figure 10:
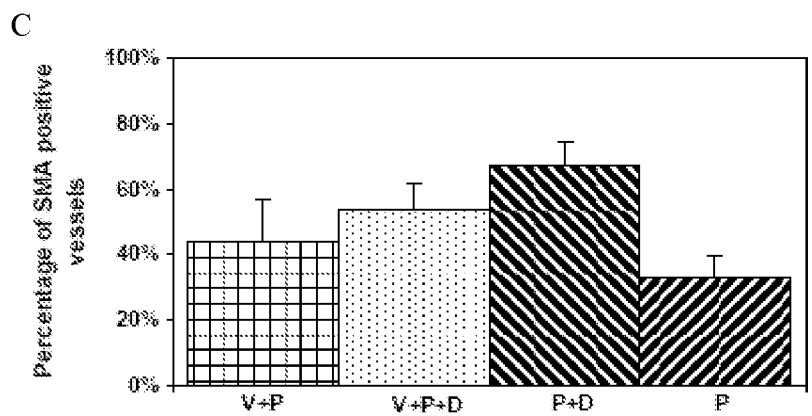
FIG. 10A is series of photomicrographs showing the effect of VEGF, DAPT, PDGF, and combinations thereof on maturation of newly formed blood vessels in the local muscle tissues around the ischemic site.
FIGS. 10B-C are bar graphs showing the effect of VEGF, DAPT, PDGF, and combinations thereof on maturation of newly formed blood vessels as measured by density of smooth muscle actin (SMA) positive vessels per unit area (FIG. 10B) and the percentage of SMA positive vessels (FIG. 10C).

The effect of controlled presentation of VEGF, PDGF and DAPT on the maturation of newly formed blood vessels was evaluated using the same in vivo ischemic type I diabetic mouse model. The result (FIGS. 10A-C) indicates that a combination of optimal level of VEGF PDGF and DAPT is superior to a combination of VEGF and PDGF in generating more matured blood vessels.

The data generated described herein indicate that compositions and methods not only reliably induce and promote angiogenesis in bodily tissues and organs but also promote and support maturation of those vessels into functional vasculature to improve blood flow to ischemic, damaged, injured, or otherwise compromised tissues and organs.

Other Embodiments

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inducing growth of new blood vessels either from existing blood vessels, or creation of de novo vessels, or a combination thereof, in a target tissue of a mammal, comprising contacting a mammalian cell by injecting into a tissue a device comprising an alginate hydrogel scaffold composition comprising N-[N-(3,5-Difluorophenacetyl-L-alanyl)]-S-phenylglycine t-butyl ester (DAPT) and vascular endothelial growth factor (VEGF), wherein said scaffold composition temporally controls release of the DAPT and the VEGF, wherein the VEGF said bioactive composition induces angiogenesis, arteriogenesis, or vasculogenesis, and wherein the VEGF comprises $VEGF_{121}$, $VEGF_{145}$, $VEGF_{165}$, $VEGF_{189}$, or $VEGF_{206}$.

2. The method of claim 1, wherein the DAPT is released before the VEGF.

3. The method of claim 1, wherein said VEGF is released over a period of weeks and said DAPT is released over a period of less than one week.

4. The method of claim 1, wherein said mammal is a human.

5. The method of claim 1, wherein said mammal has diabetes.

6. The method of claim 1, wherein said hydrogel scaffold comprises nanopores.

7. The method of claim 1, wherein the DAPT is released from the scaffold composition at a first rate and the VEGF is released from the scaffold composition at a second rate, and wherein the second rate is slower than the first rate.

8. The method of claim 7, wherein the VEGF exits from the scaffold composition for a time period of one or more weeks.

9. The method of claim 7, wherein the DAPT exits from the scaffold composition for a period of one or more days.

10. The method of claim 1, wherein the device comprises a molar ratio of 1:1 to 1:200 for $VEGF_{165}$ to DAPT.

11. The method of claim 10, wherein the device comprises a molar ratio of 1:31 for $VEGF_{165}$ to DAPT.

12. The method of claim 1, wherein the mammal has coronary arterial disease (CAD) or peripheral arterial disease (PAD).

13. The method of claim 1, wherein the mammal has acute or chronic ischemia due to peripheral arterial disease (PAD).

14. The method of claim 1, wherein the mammal has a diabetic ulcer or a wound due to peripheral arterial disease (PAD).

15. A method of inducing growth of new blood vessels either from existing blood vessels, or creation of de novo vessels, or a combination thereof, in a target tissue of a mammal, comprising contacting a mammalian cell by injecting into a tissue a device comprising an alginate hydrogel scaffold composition comprising N-[N-(3,5-Difluorophenacetyl-L-alanyl)]-S-phenylglycine t-butyl ester (DAPT) and a bioactive composition selected from the group consisting of vascular endothelial growth factor (VEGF) and platelet-derived growth factor (PDGF), wherein said scaffold composition temporally controls release of the DAPT and the bioactive composition, wherein the bioactive composition induces angiogenesis, arteriogenesis, or vasculogenesis, and wherein the VEGF comprises $VEGF_{121}$, $VEGF_{145}$, $VEGF_{165}$, $VEGF_{189}$, or $VEGF_{206}$.

16. The method of claim 15, wherein said DAPT is released within 1-3 days and said VEGF or PDGF is released within 7-60 days.

17. The method of claim 15, wherein the DAPT is released before the bioactive composition.

18. The method of claim 15, wherein the PDGF comprises PDGF-BB.

19. The method of claim 15, wherein the device comprises a molar ratio of 1:1 to 1:200 for $VEGF_{165}$ to DAPT, or 1:1 to 1:200 for PDGF-BB to DAPT.

20. The method of claim 19, wherein the device comprises a molar ratio of 1.8:31 for PDGF-BB to DAPT.

21. The method of claim 15, wherein the mammal has coronary arterial disease (CAD) or peripheral arterial disease (PAD).

22. The method of claim 15, wherein the mammal has acute or chronic ischemia due to peripheral arterial disease (PAD).

23. The method of claim 15, wherein the mammal has a diabetic ulcer or a wound due to peripheral arterial disease (PAD).

24. A method of inducing growth of new blood vessels either from existing blood vessels, or creation of de novo vessels, or a combination thereof, in a target tissue of a mammal, comprising contacting a mammalian cell by injecting into a tissue a device comprising a hydrogel scaffold composition comprising N-[N-(3,5-Difluorophenacetyl-L-alanyl)]-S-phenylglycine t-butyl ester (DAPT), vascular endothelial growth factor (VEGF), and platelet-derived growth factor (PDGF), wherein said scaffold composition temporally controls release of the DAPT, VEGF, and PDGF, and wherein the VEGF and PDGF induce angiogenesis, arteriogenesis, or vasculogenesis.

25. The method of claim 24, wherein the device comprises a molar ratio of 1:0.1:1 to 1:10:200 for $VEGF_{165}$, PDGF-BB and DAPT.

26. The method of claim 25, wherein the device comprises a molar ratio of 1:1.8:31 for $VEGF_{165}$, PDGF-BB and DAPT.

27. The method of claim 24, wherein the mammal has coronary arterial disease (CAD) or peripheral arterial disease (PAD).

28. The method of claim 24, wherein the mammal has acute or chronic ischemia due to peripheral arterial disease (PAD).

29. The method of claim 24, wherein the mammal has a diabetic ulcer or a wound due to peripheral arterial disease (PAD).

\* \* \* \* \*